US012558177B2

(12) United States Patent
Sanchez et al.

(10) Patent No.: US 12,558,177 B2
(45) Date of Patent: Feb. 24, 2026

(54) LOCKING CASTERS FOR SURGICAL SYSTEMS WITH SENSING

(71) Applicant: Auris Health, Inc., Redwood City, CA (US)

(72) Inventors: Jessie Ramirez Sanchez, San Jose, CA (US); Liam J. Nolan, Salt Lake City, UT (US); Christian De Jesus Ruiz, Liberty Hill, TX (US); Sarah Ann Horton, San Jose, CA (US)

(73) Assignee: Auris Health, Inc., Redwood, CA (US)

( * ) Notice: Subject to any disclaimer, the term of this patent is extended or adjusted under 35 U.S.C. 154(b) by 243 days.

(21) Appl. No.: 18/312,911

(22) Filed: May 5, 2023

(65) Prior Publication Data

US 2023/0390010 A1     Dec. 7, 2023

Related U.S. Application Data

(60) Provisional application No. 63/350,001, filed on Jun. 7, 2022.

(51) Int. Cl.
    *A61B 34/00*     (2016.01)
    *A61B 34/20*     (2016.01)
    (Continued)

(52) U.S. Cl.
    CPC .............. *A61B 34/37* (2016.02); *A61B 34/20* (2016.02); *A61B 34/70* (2016.02); *A61B 34/75* (2016.02);
    (Continued)

(58) Field of Classification Search
    CPC ......... A61B 34/37; A61B 34/20; A61B 34/70;
    A61B 34/75; A61B 90/361; A61B 2017/00973; A61B 2034/2051; A61B 2034/2059; A61B 2034/2065; A61B 2034/301; A61B 2034/105;
    (Continued)

(56) References Cited

U.S. PATENT DOCUMENTS 9,409,753 B2     8/2016   Kobuss
9,763,741 B2     9/2017   Alvarez et al.
(Continued)

FOREIGN PATENT DOCUMENTS

JP      2016154736 A     9/2016
KR     101600367 B1     3/2016
(Continued)

OTHER PUBLICATIONS

PCT International Search Report; Application No. PCT/IB2023/055878; Sep. 25, 2023; 6 pages.
(Continued)

*Primary Examiner* — Sohana Tanju Khayer
(74) *Attorney, Agent, or Firm* — FBT Gibbons LLP

(57) ABSTRACT

A caster assembly that includes a caster wheel, a lock member, a pedal, and a position sensor. The lock member can engage the caster wheel. Movement of the pedal towards a depressed position can cause engagement of the lock member against the caster wheel to resist or prevent rotation of the caster wheel. Movement of the pedal towards a released position can separate the lock member from the caster wheel to permit rotation of the caster wheel. The position sensor can detect a position of the pedal.

20 Claims, 34 Drawing Sheets

(51) Int. Cl.

| | |
|---|---|
| *A61B 34/30* | (2016.01) |
| *A61B 34/37* | (2016.01) |
| B60B 33/00 | (2006.01) |
| *A61B 17/00* | (2006.01) |
| *A61B 90/00* | (2016.01) |

(52) U.S. Cl.
CPC .................... B60B 33/0078 (2013.01); *A61B 2017/00973* (2013.01); *A61B 2034/2051* (2016.02); *A61B 2034/2059* (2016.02); *A61B 2034/2065* (2016.02); *A61B 2034/301* (2016.02); *A61B 90/361* (2016.02)

(58) Field of Classification Search
CPC ........ A61B 2034/2061; B60B 33/0078; B60B 33/0092; B60B 33/026; A61G 13/04; A61G 13/104
See application file for complete search history.

(56) References Cited

U.S. PATENT DOCUMENTS

| | | | | |
|---|---|---|---|---|
| 2012/0316473 | A1* | 12/2012 | Bonutti ................. | A61B 90/06 601/2 |
| 2017/0333141 | A1* | 11/2017 | Itkowitz ................ | A61G 13/02 |
| 2018/0015926 | A1* | 1/2018 | Cunningham ...... | B60W 10/026 |
| 2020/0072641 | A1 | 3/2020 | Zhao et al. | |
| 2020/0128598 | A1* | 4/2020 | Keller ..................... | H04L 67/12 |
| 2021/0038335 | A1* | 2/2021 | Maret .................... | A61B 34/74 |
| 2022/0008152 | A1* | 1/2022 | Rohr Daniel ......... | A61B 34/25 |
| 2022/0009474 | A1* | 1/2022 | Zhao ..................... | B60W 10/06 |
| 2022/0034400 | A1* | 2/2022 | Miller .................. | F16H 63/304 |
| 2022/0104915 | A1 | 4/2022 | Iceman et al. | |
| 2022/0134547 | A1* | 5/2022 | Cristache .............. | B25J 11/008 700/245 |
| 2022/0354604 | A1* | 11/2022 | Fischer .................. | A61B 34/71 |
| 2022/0401161 | A1* | 12/2022 | Chappuis .............. | A61B 90/50 |
| 2023/0038537 | A1* | 2/2023 | Baker, Jr. ........... | B60B 33/0092 |
| 2023/0160775 | A1* | 5/2023 | Yuds ...................... | A61M 1/28 604/29 |
| 2023/0174051 | A1* | 6/2023 | Goossens .............. | B60K 17/28 |
| 2025/0072985 | A1* | 3/2025 | Xi .......................... | F16M 11/42 |

FOREIGN PATENT DOCUMENTS

| | | |
|---|---|---|
| KR | 101988695 B1 | 6/2019 |
| WO | 2017040988 A1 | 3/2017 |

OTHER PUBLICATIONS

PCT Written Opinion of the International Searching Authority; Application No. PCT/IB2023/055878; Sep. 25, 2023; 7 pages.

* cited by examiner

LOCKING CASTERS FOR SURGICAL SYSTEMS WITH SENSING

CROSS-REFERENCE TO RELATED APPLICATIONS

This application claims priority to U.S. Provisional Application No. 63/350,001 filed Jun. 7, 2022 and entitled, "Locking Casters for Surgical Systems with Sensing", which is incorporated by reference herein as if reproduced in its entirety.

TECHNICAL FIELD

Systems and methods disclosed herein related to surgical systems, and more particularly to systems to transport surgical systems.

BACKGROUND

Minimally invasive procedures allow for access to a targeted site within a patient with minimal trauma to the patient. For example, laparoscopic surgery can allow for surgical access to a patient's cavity through a small incision on the patient's abdomen. A cannula can form a surgical corridor to allow tools to access the patient's cavity. In some procedures, the cannula can be coupled to a robotic arm to allow the robotic arm to rotate, pivot, or otherwise move the cannula within the patient's cavity. By moving the cannula within the patient's cavity, tools operatively coupled to the robotic arm can access desired portions of the patient's cavity. In some applications, the cannula can be attached and/or detached from the robotic arm to facilitate positioning, configuration, and/or sterilization of the cannula.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
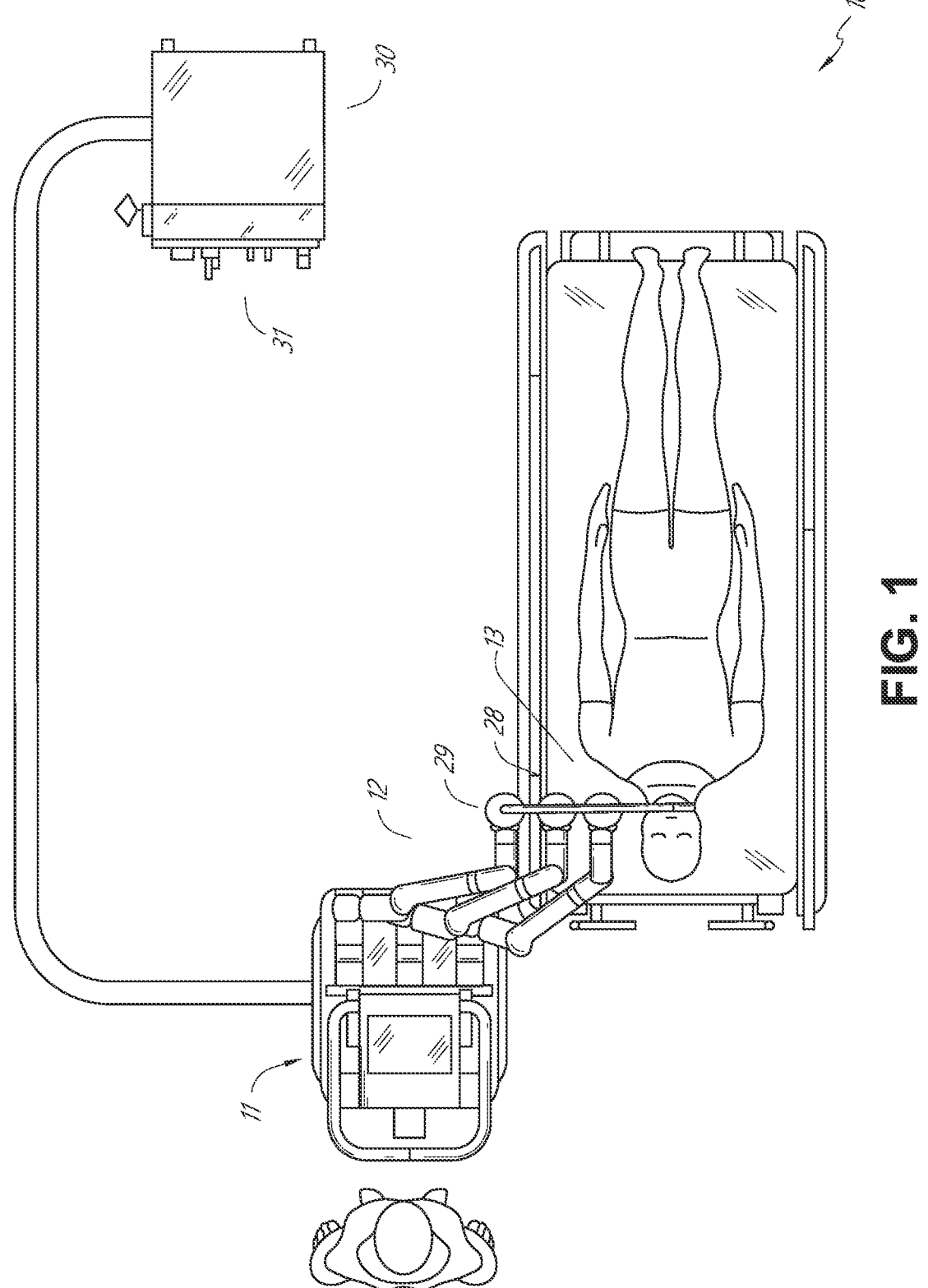
FIG. 1 illustrates an embodiment of a cart-based robotic system arranged for diagnostic and/or therapeutic bronchoscopy procedure(s).
Figure 2:
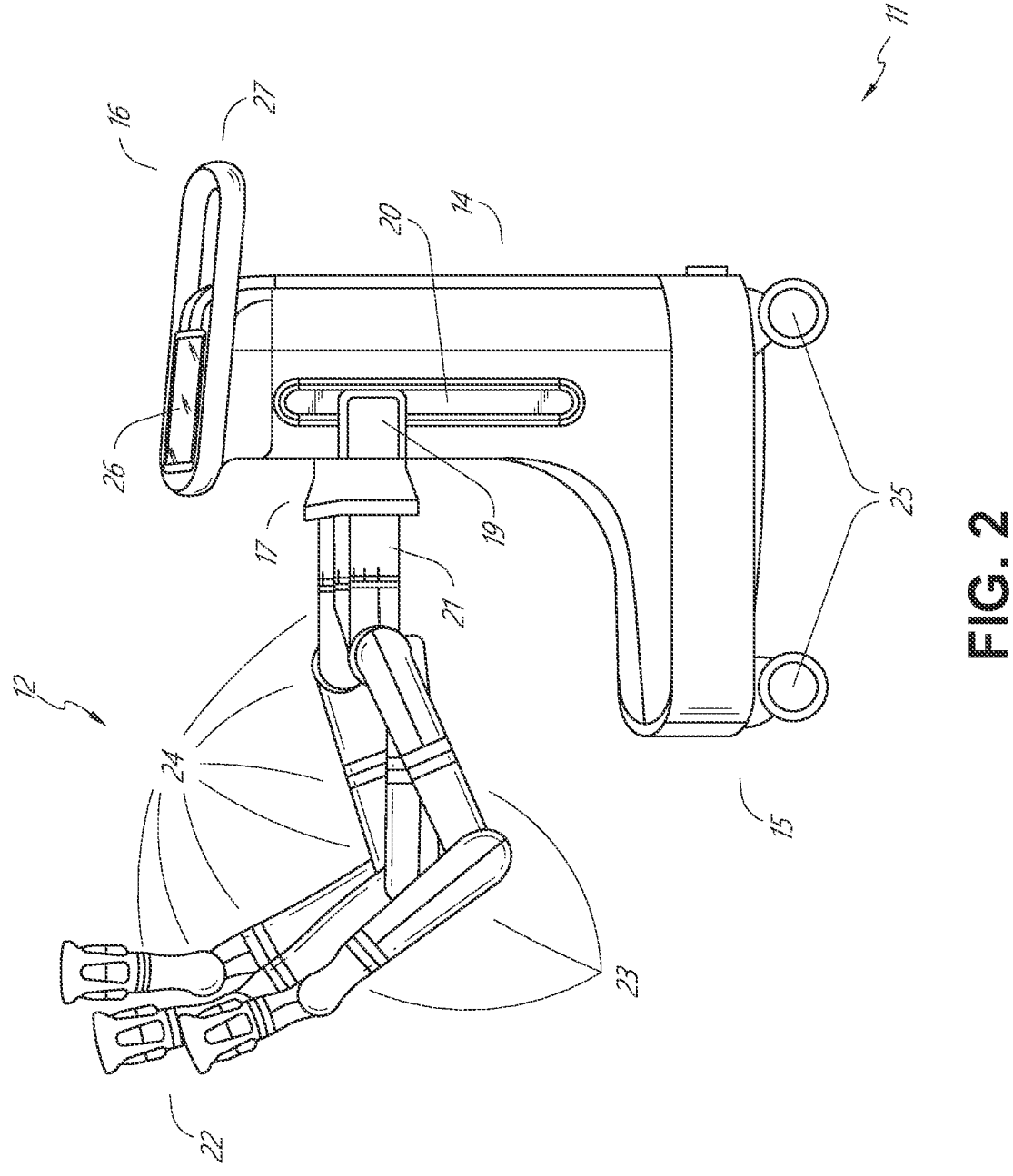
FIG. 2 depicts further aspects of the robotic system of FIG. 1.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
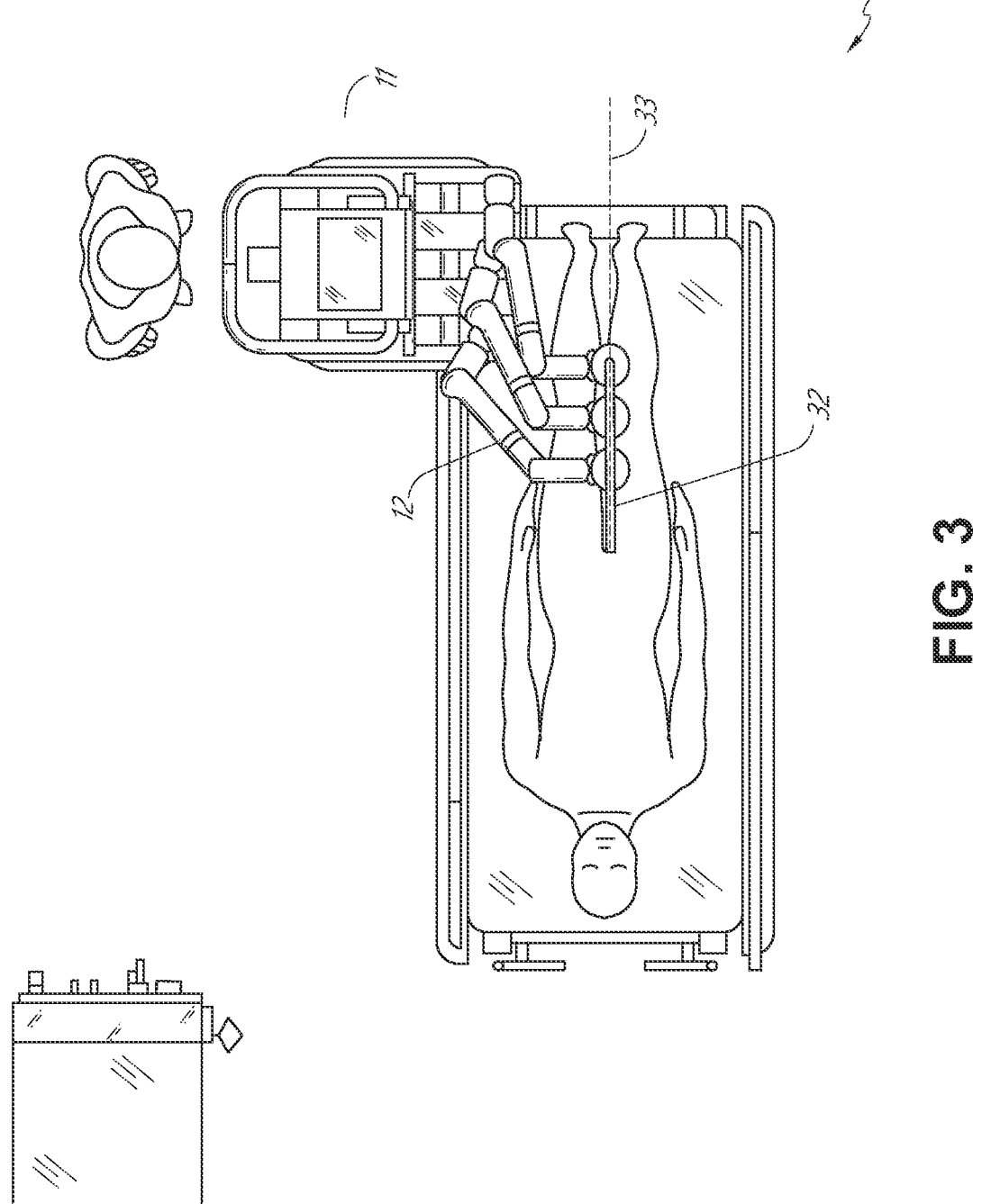
FIG. 3 illustrates an embodiment of the robotic system of FIG. 1 arranged for ureteroscopy.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
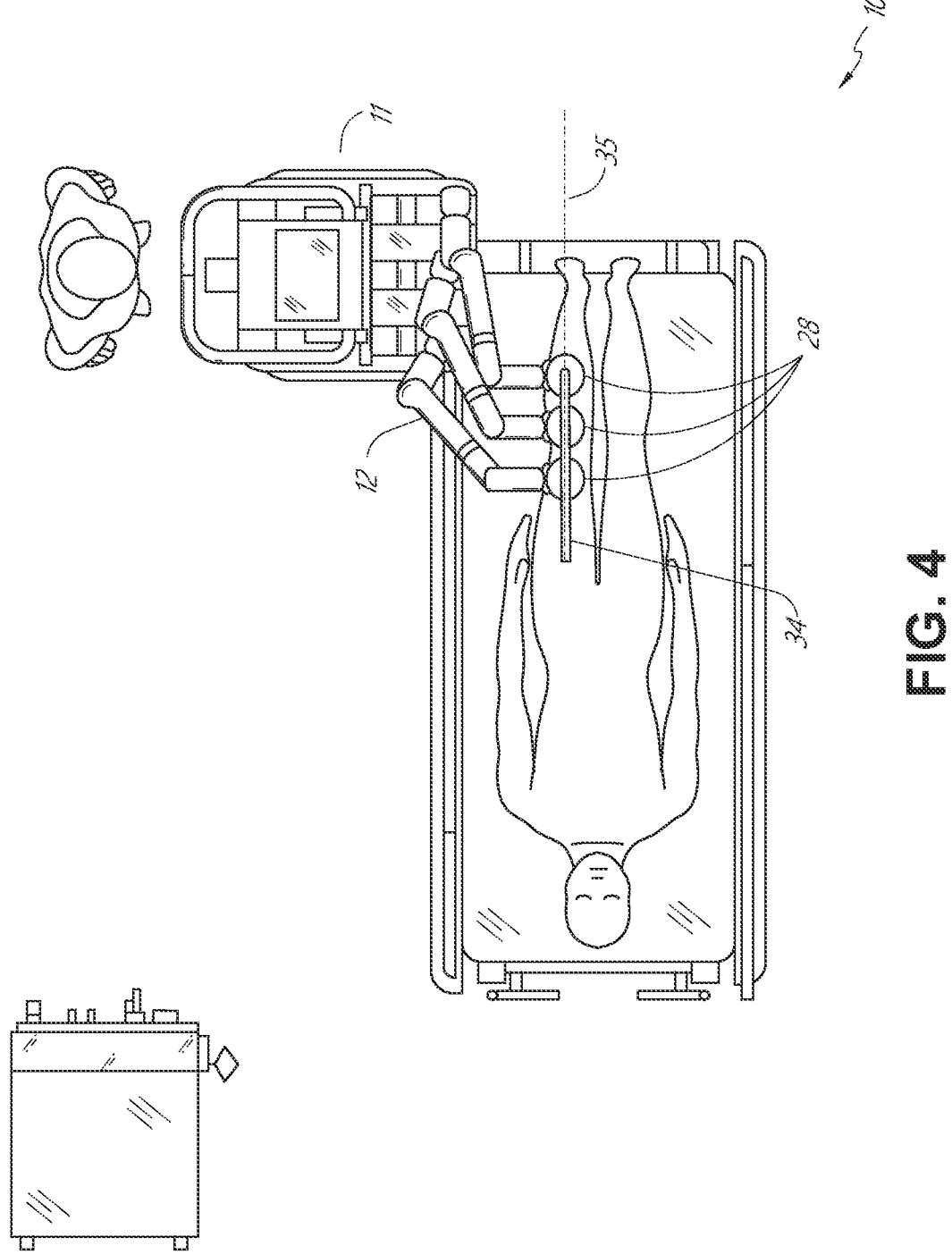
FIG. 4 illustrates an embodiment of the robotic system of FIG. 1 arranged for a vascular procedure.

FIG. 4 illustrates an embodiment of a robotically enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
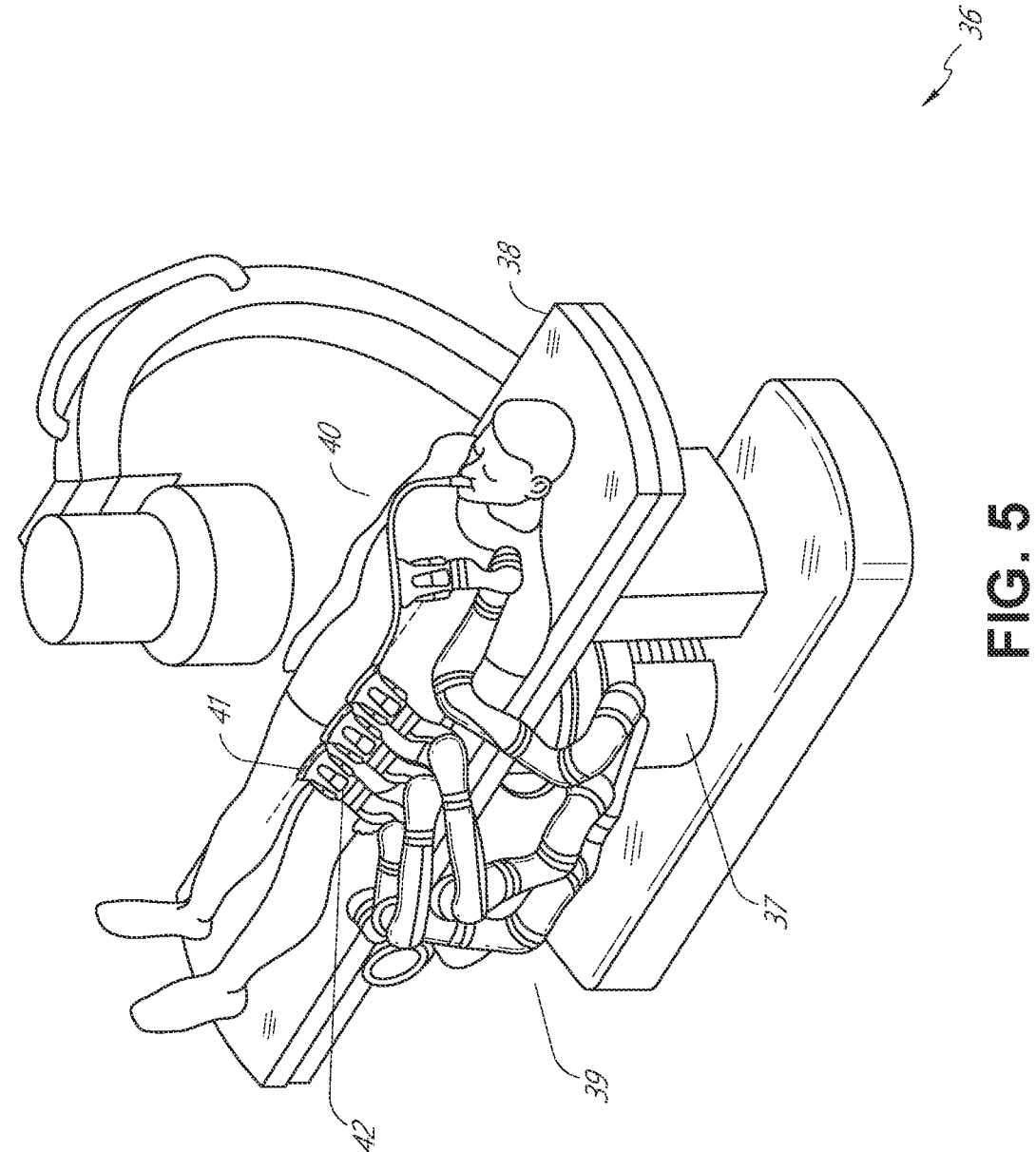
FIG. 5 illustrates an embodiment of a table-based robotic system arranged for a bronchoscopy procedure.

Embodiments of the robotically enabled medical system may also incorporate the patient's table. Incorporation of the table reduces the amount of capital equipment within the operating room by removing the cart, which allows greater access to the patient. FIG. 5 illustrates an embodiment of such a robotically enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
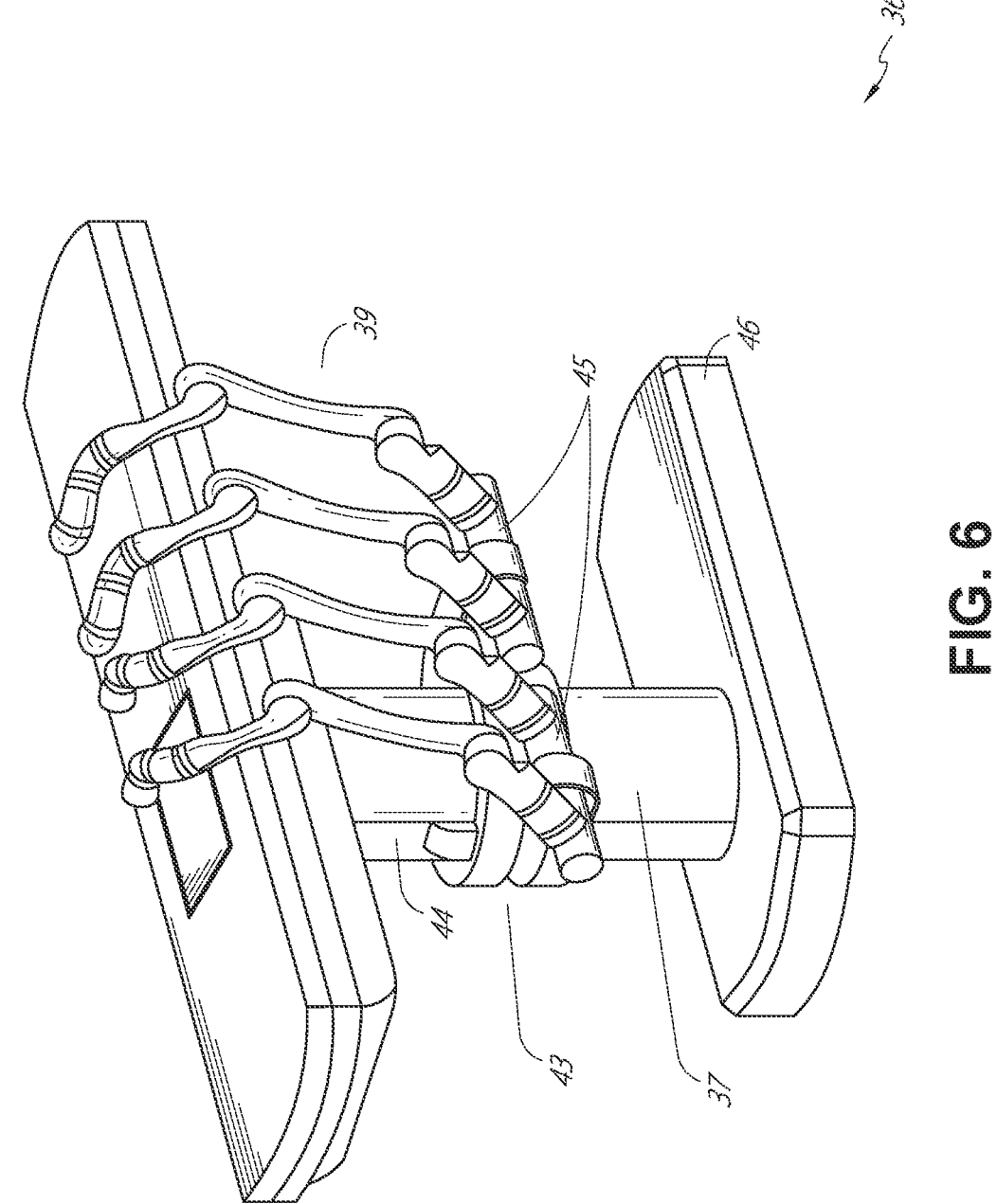
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
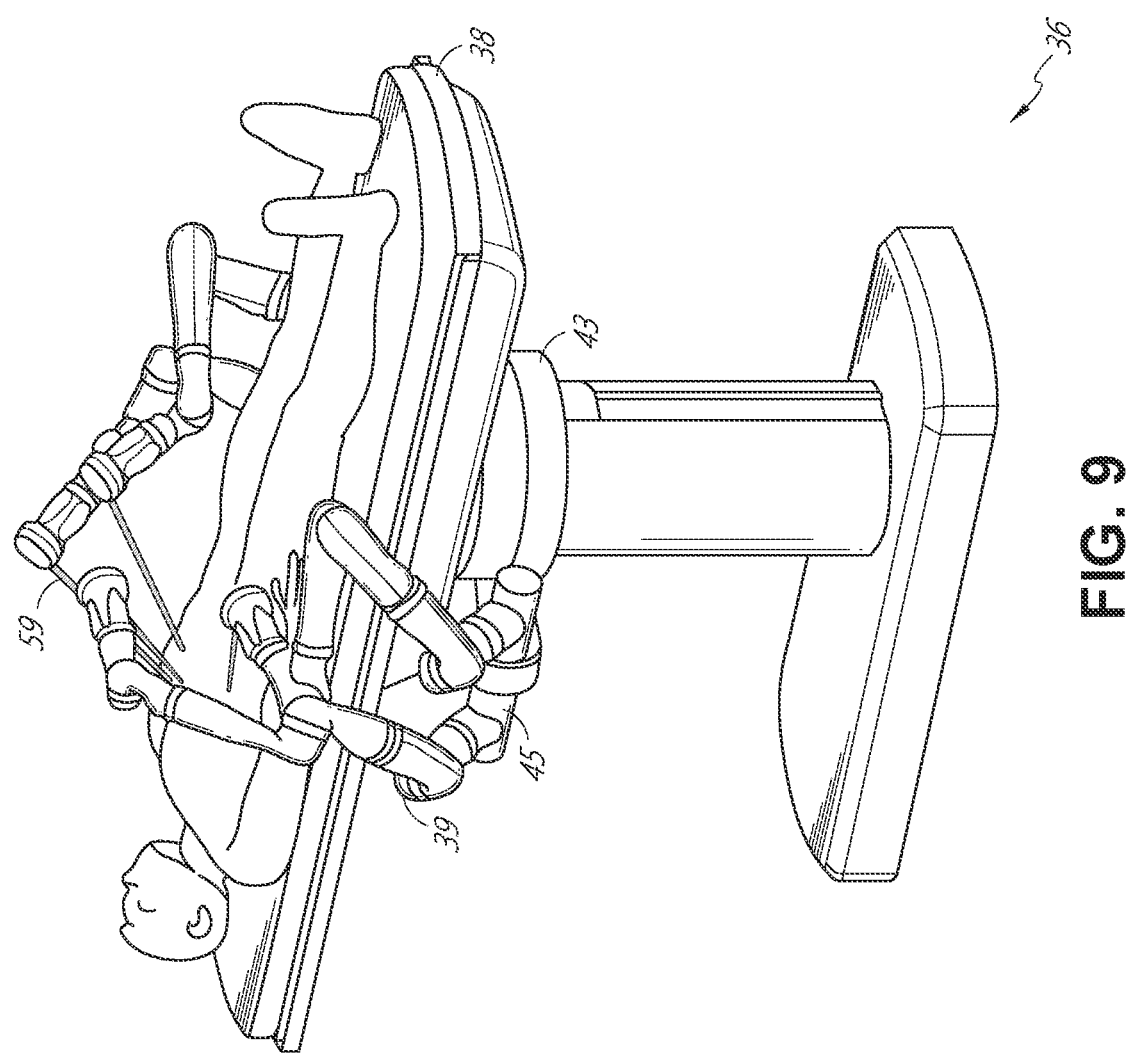
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
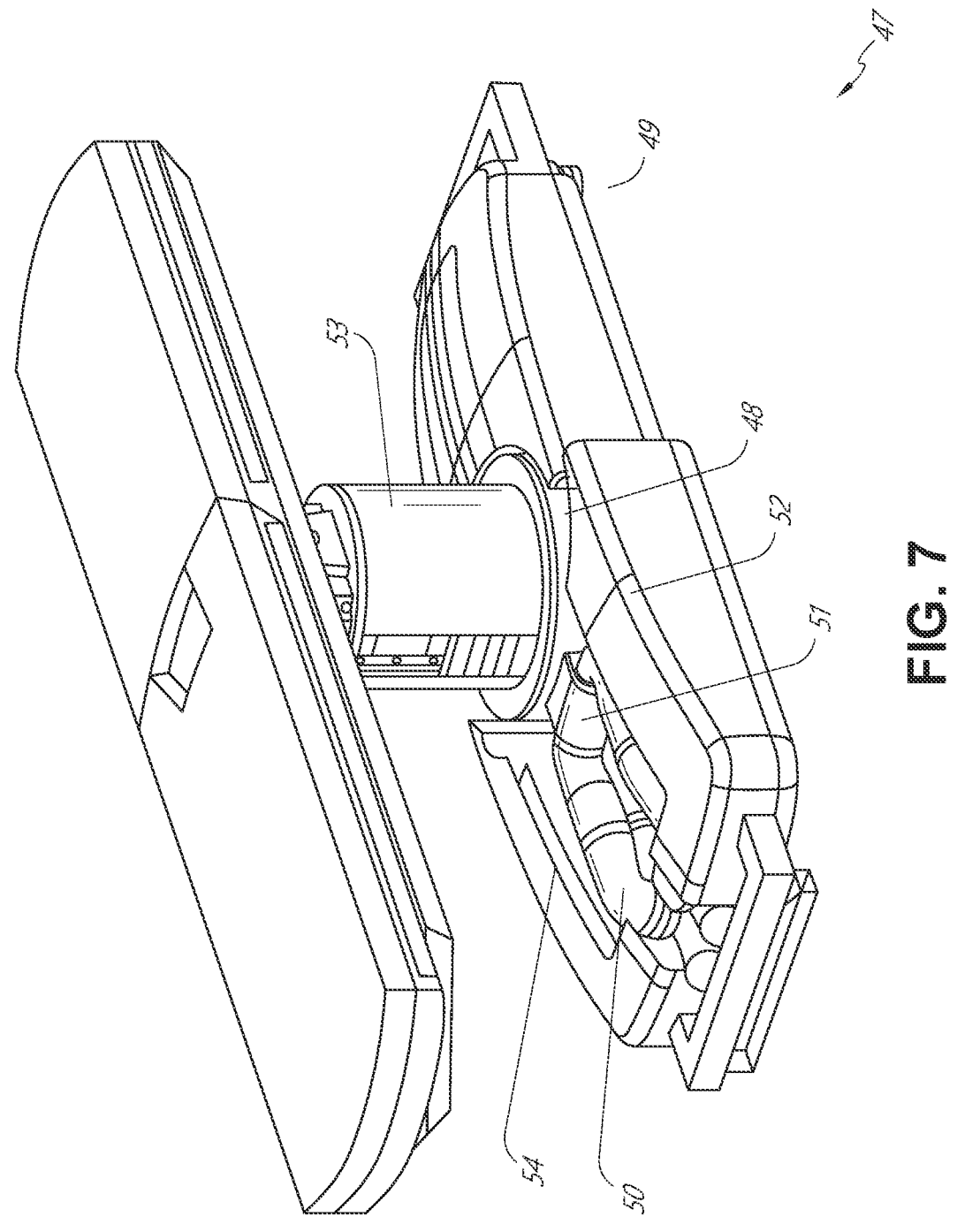
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
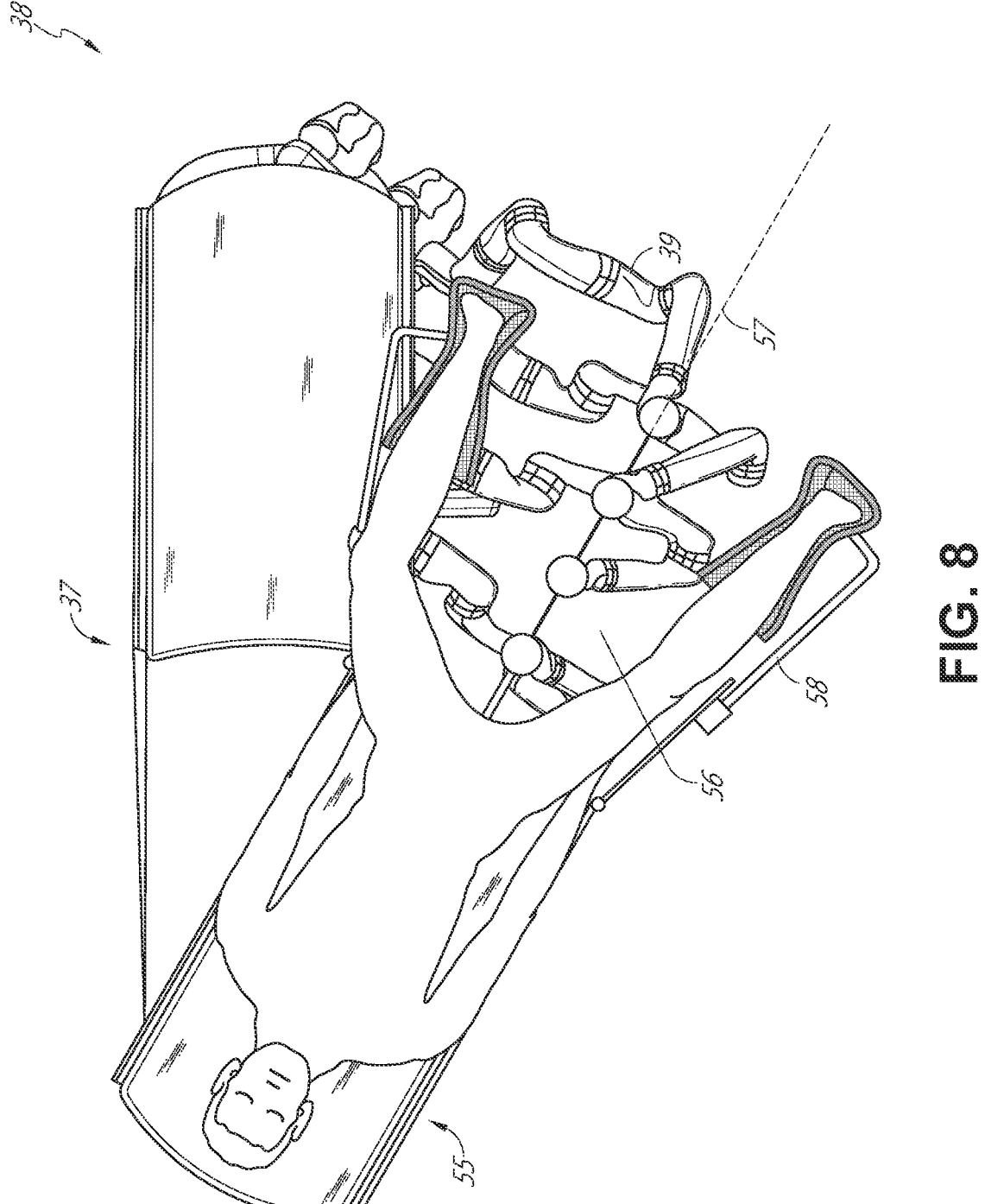
FIG. 8 illustrates an embodiment of a table-based robotic system configured for a ureteroscopy procedure.

FIG. 8 illustrates an embodiment of a robotically enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
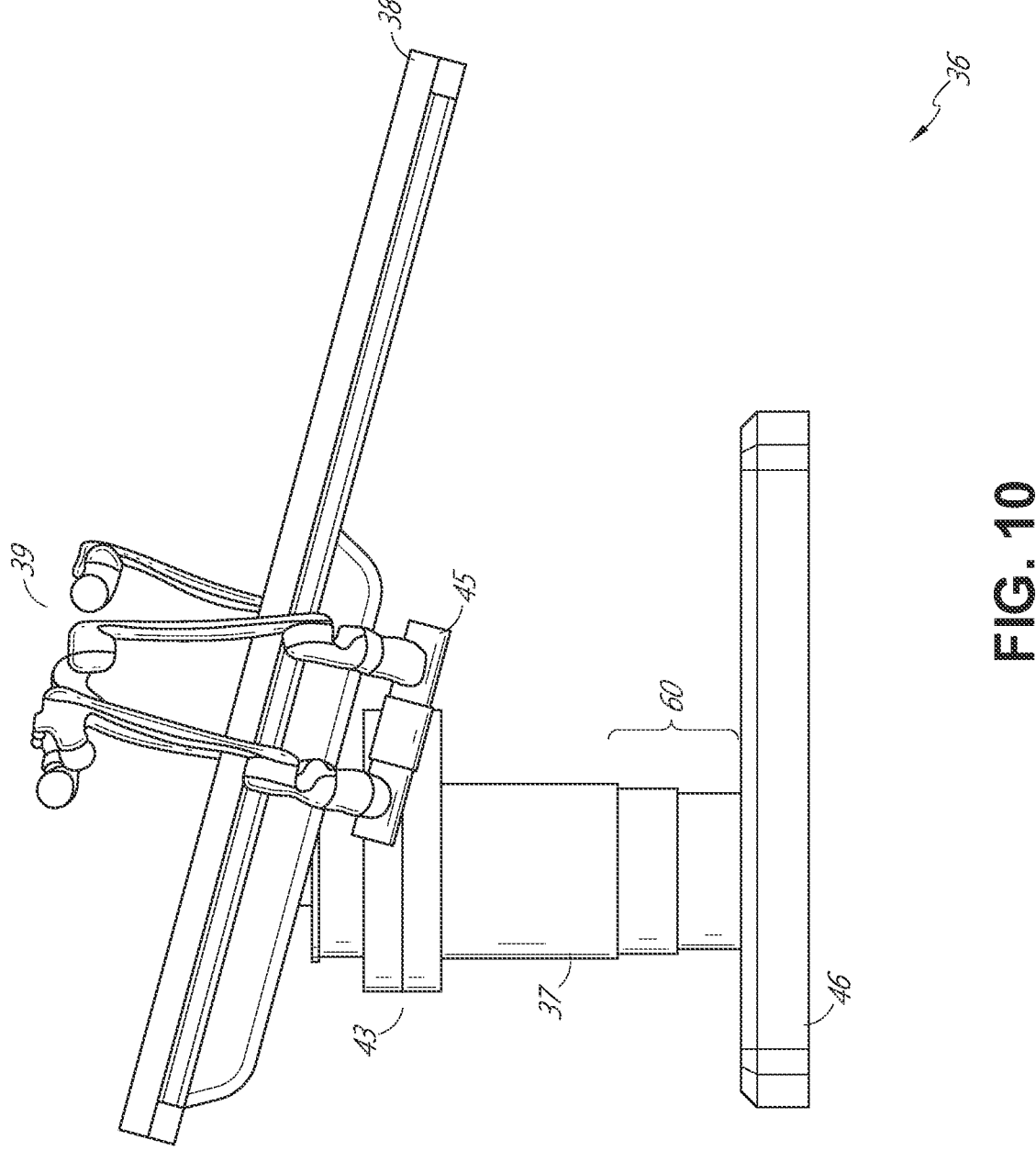
FIG. 10 illustrates an embodiment of the table-based robotic system of FIGS. 5-9 with pitch or tilt adjustment.

To accommodate laparoscopic procedures, the robotically enabled table system may also tilt the platform to a desired angle. FIG. 10 illustrates an embodiment of the robotically enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
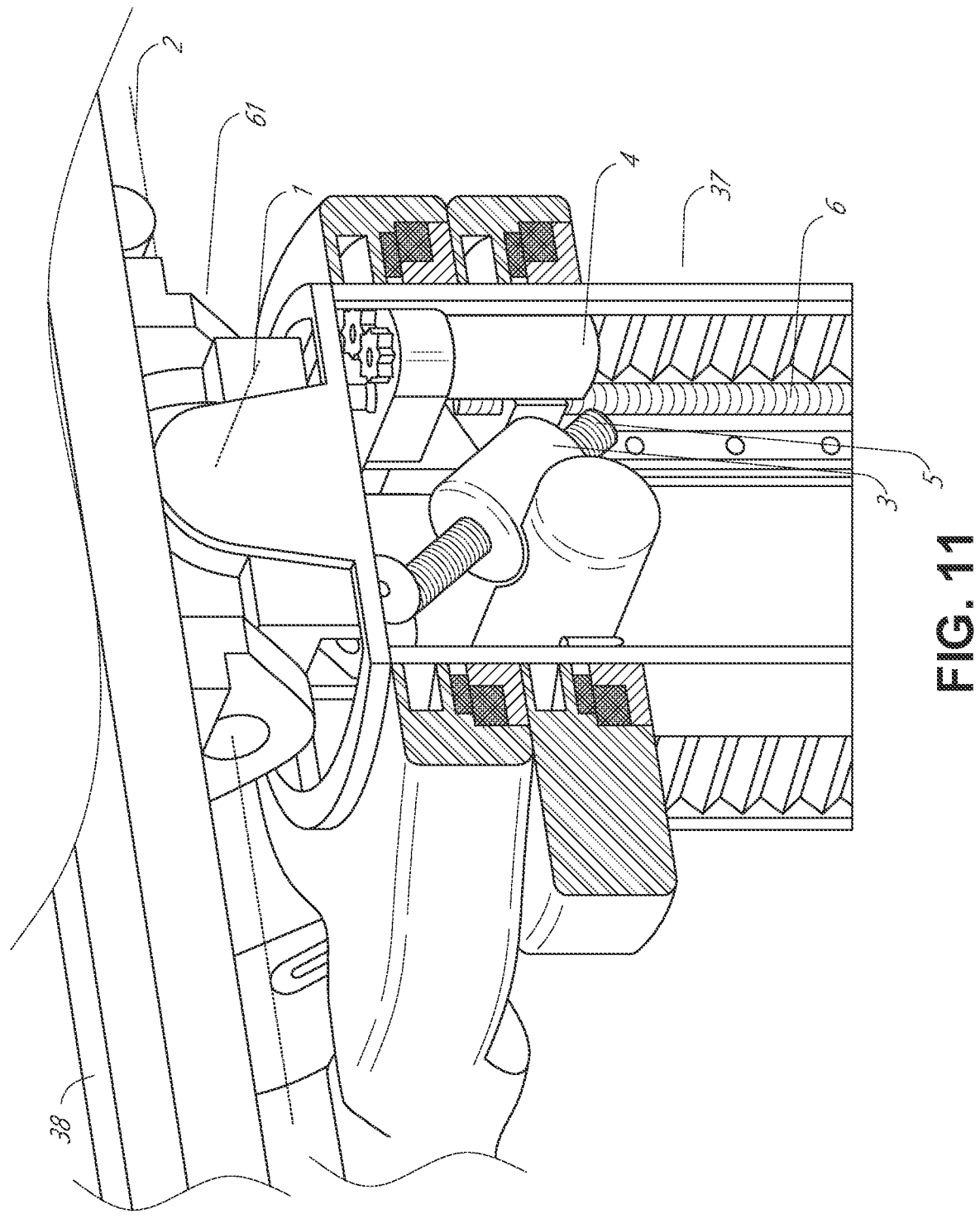
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
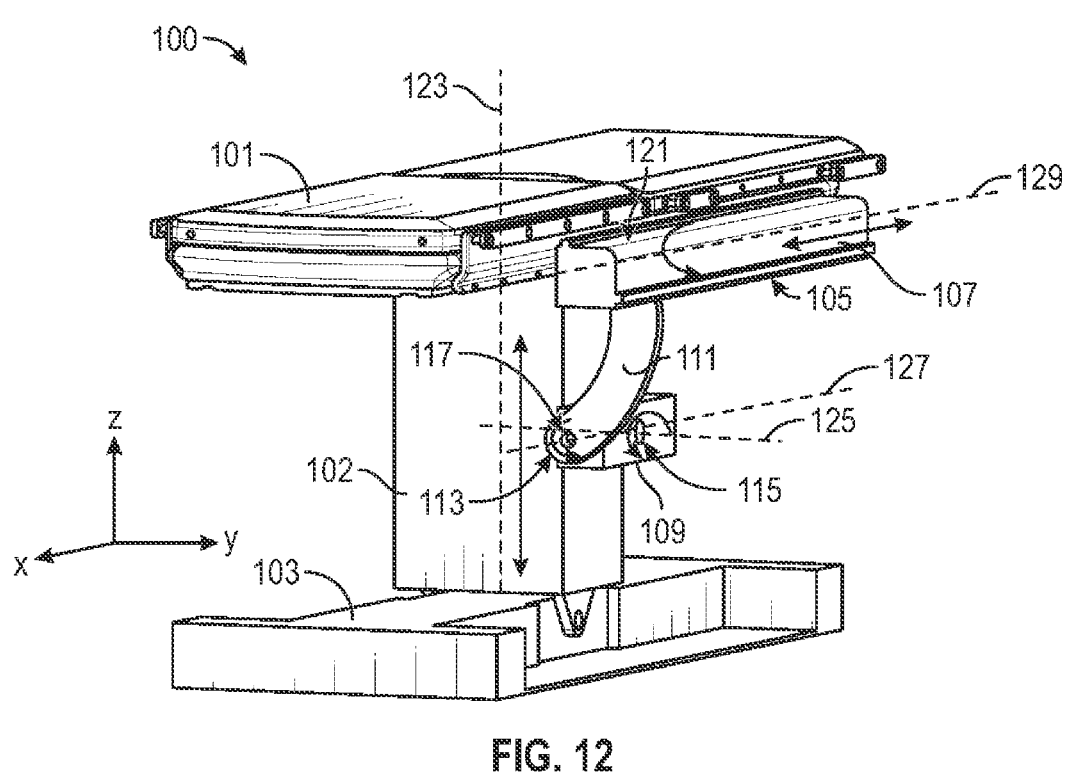
FIG. 12 illustrates an alternative embodiment of a table-based robotic system.
Figure 13:
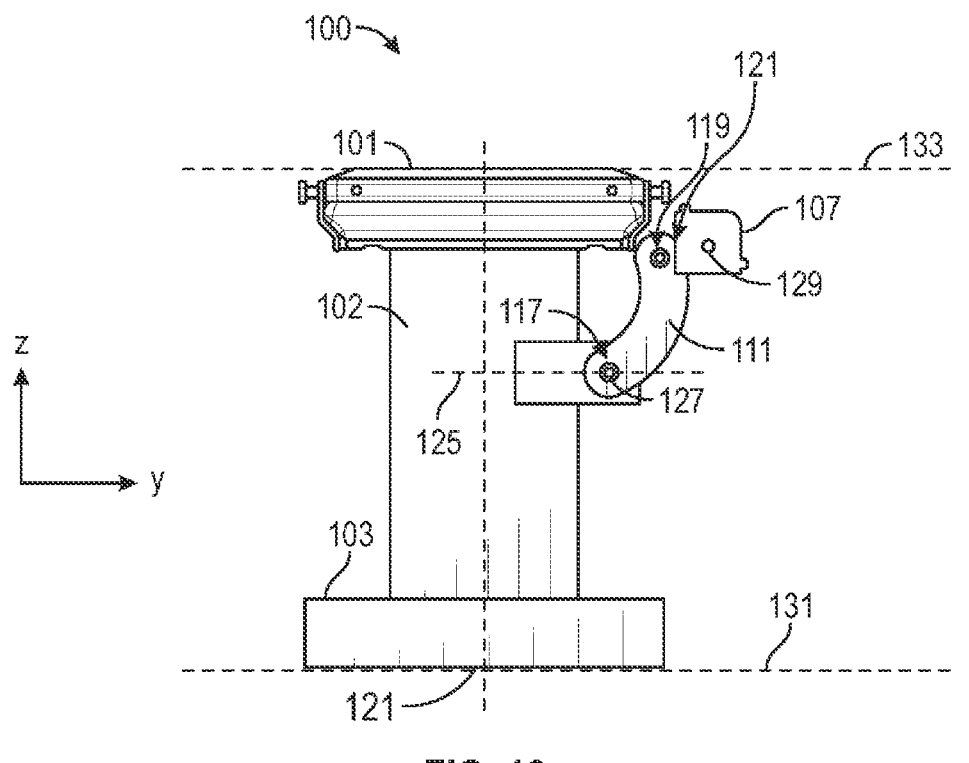
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
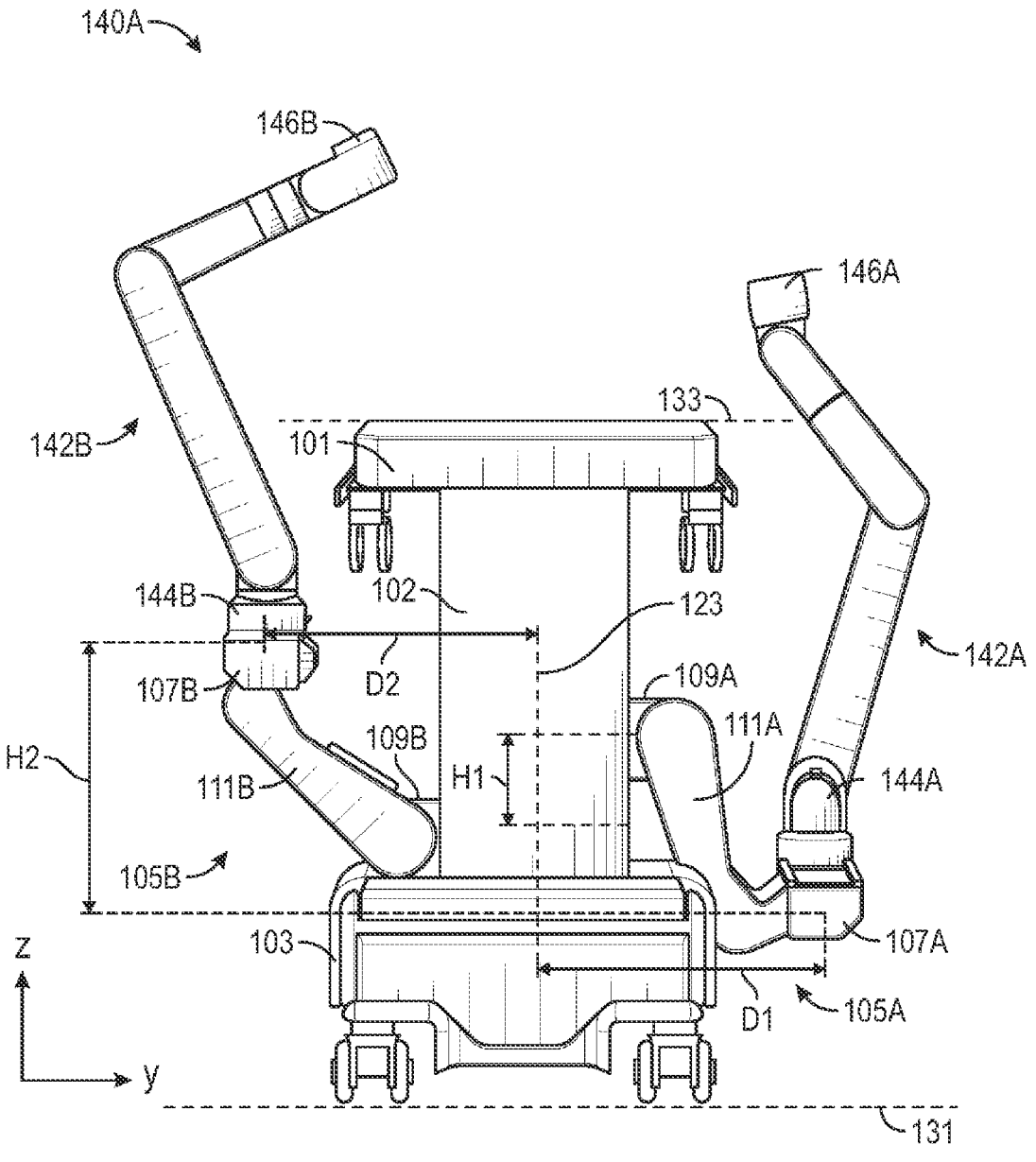
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (one degree of freedom, including insertion), a wrist (three degrees of freedom, including wrist pitch, yaw, and roll), an elbow (one degree of freedom, including elbow pitch), a shoulder (two degrees of freedom, including shoulder pitch and yaw), and base 144A, 144B (one degree of freedom, including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
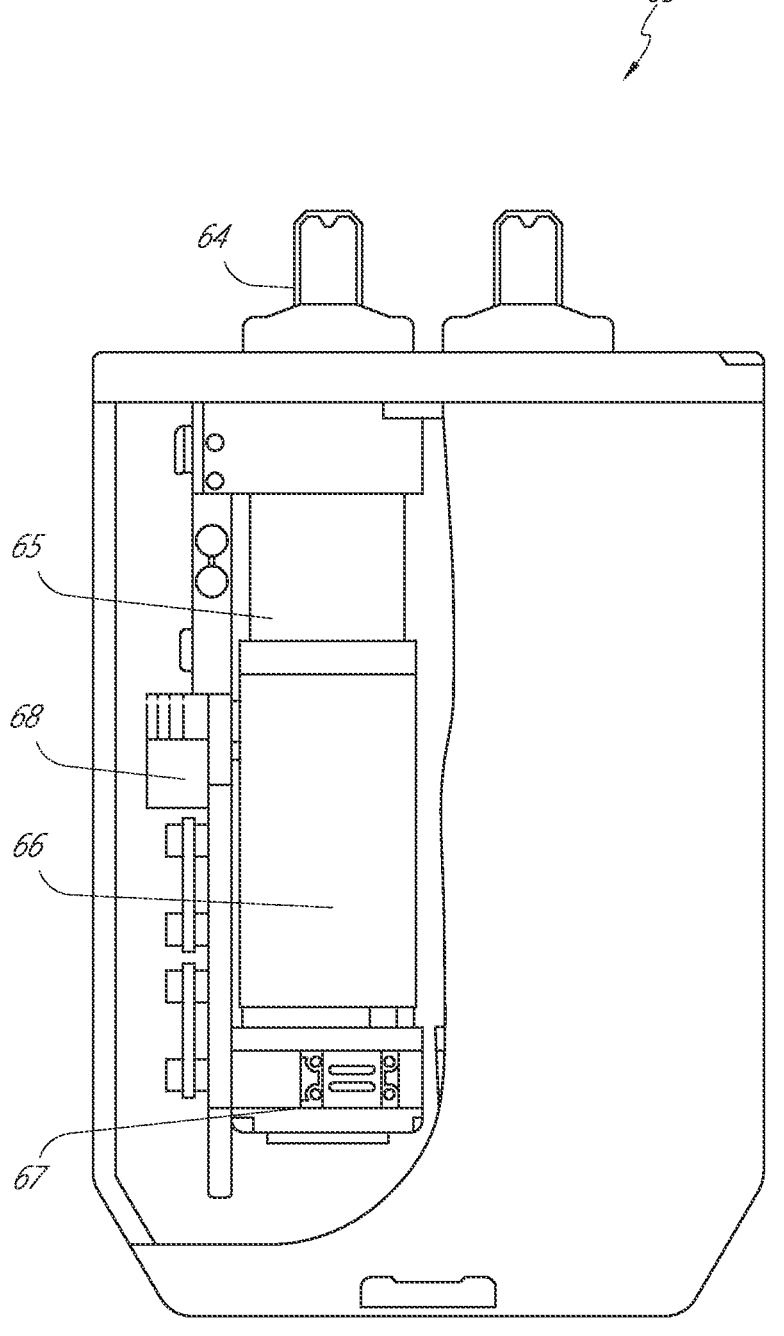
FIG. 15 illustrates an exemplary instrument driver.
Figure 15:

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
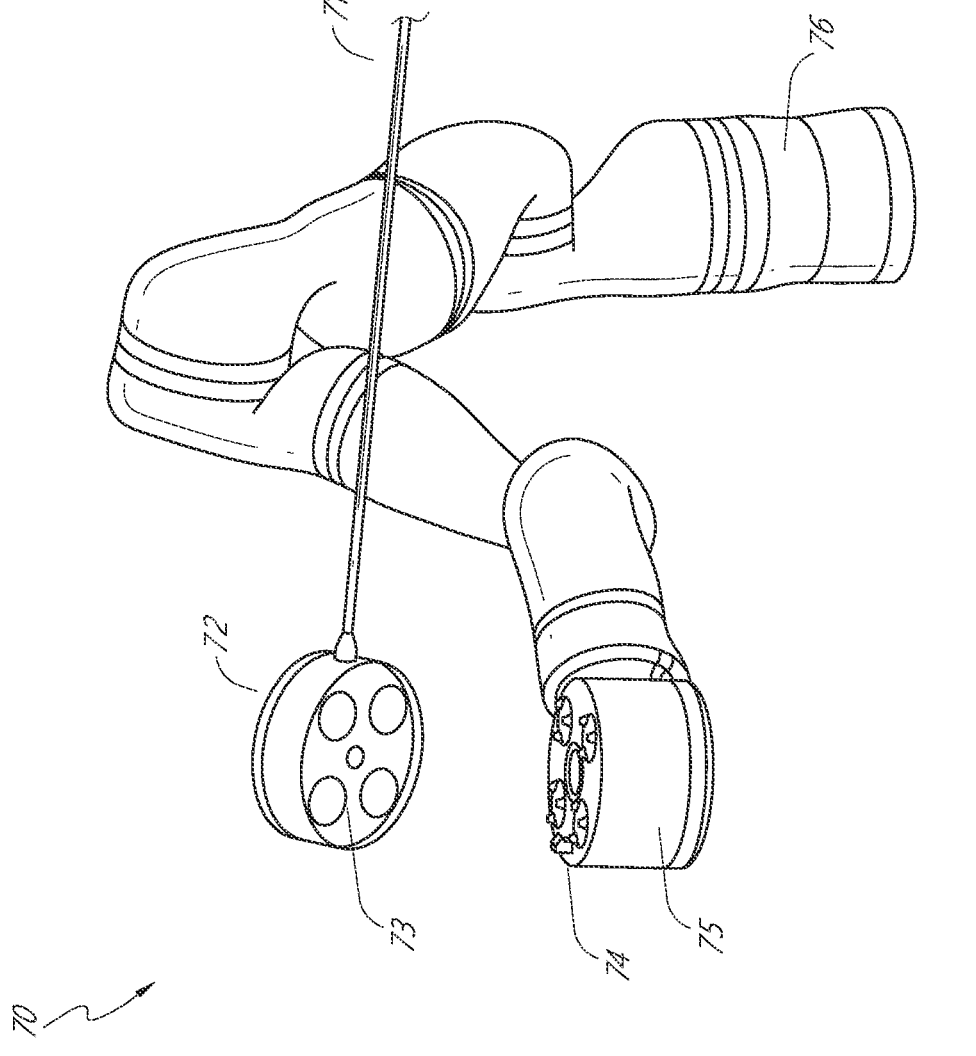
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
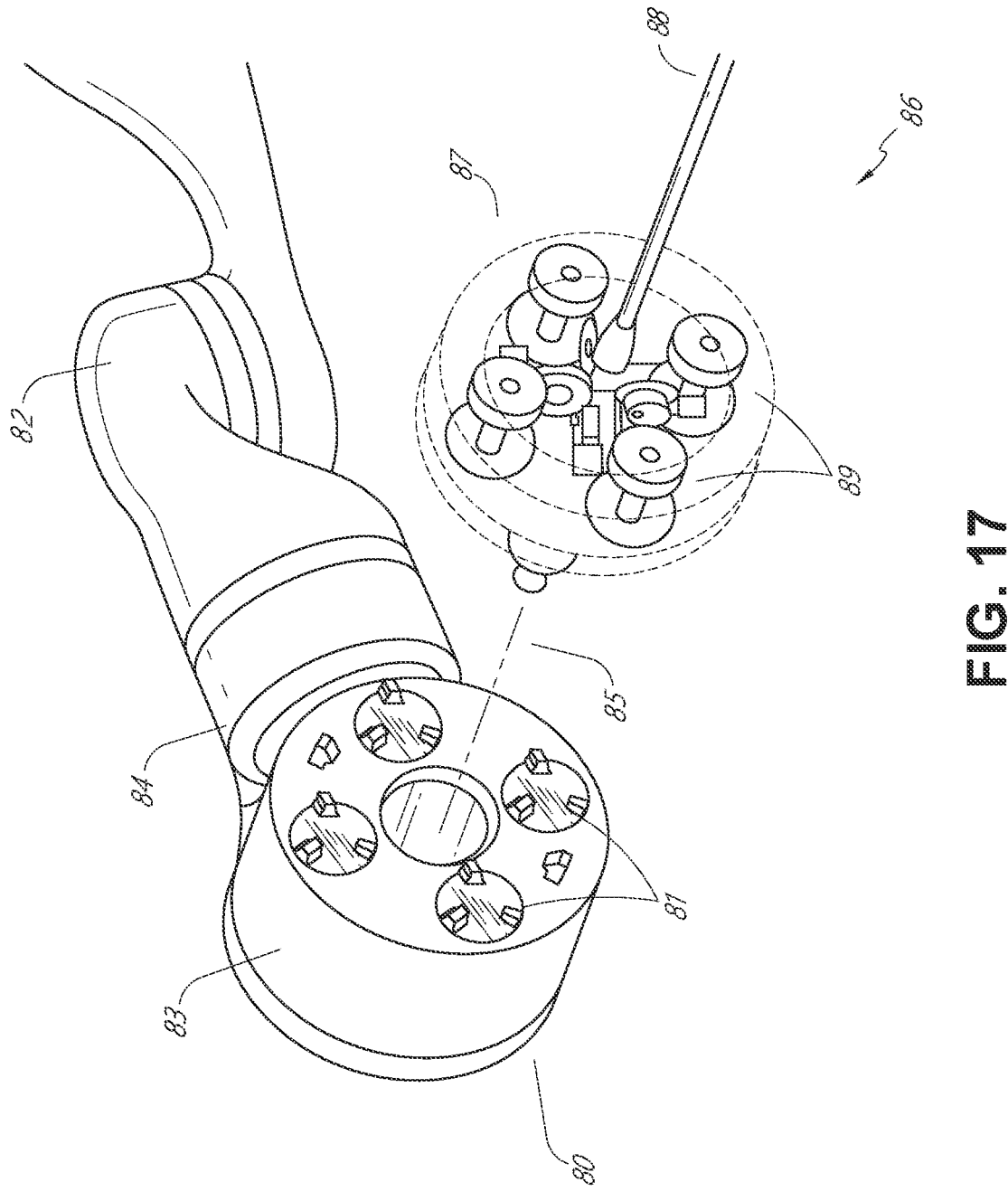
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
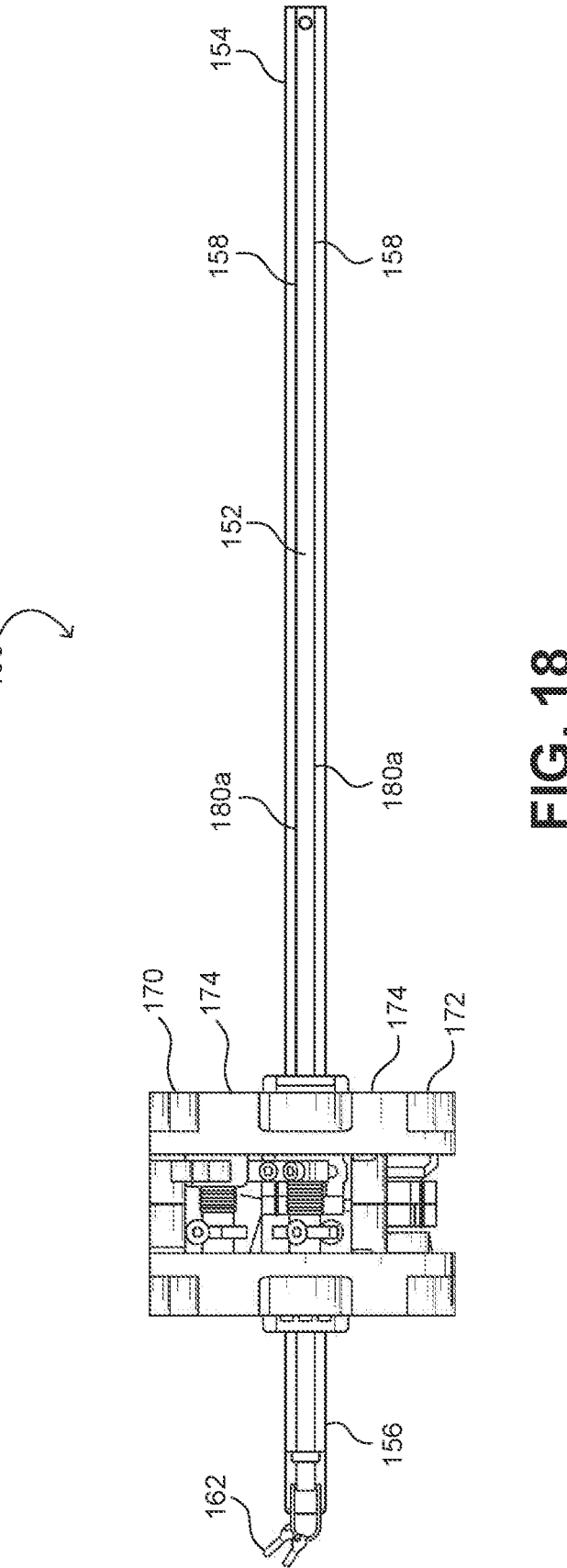
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
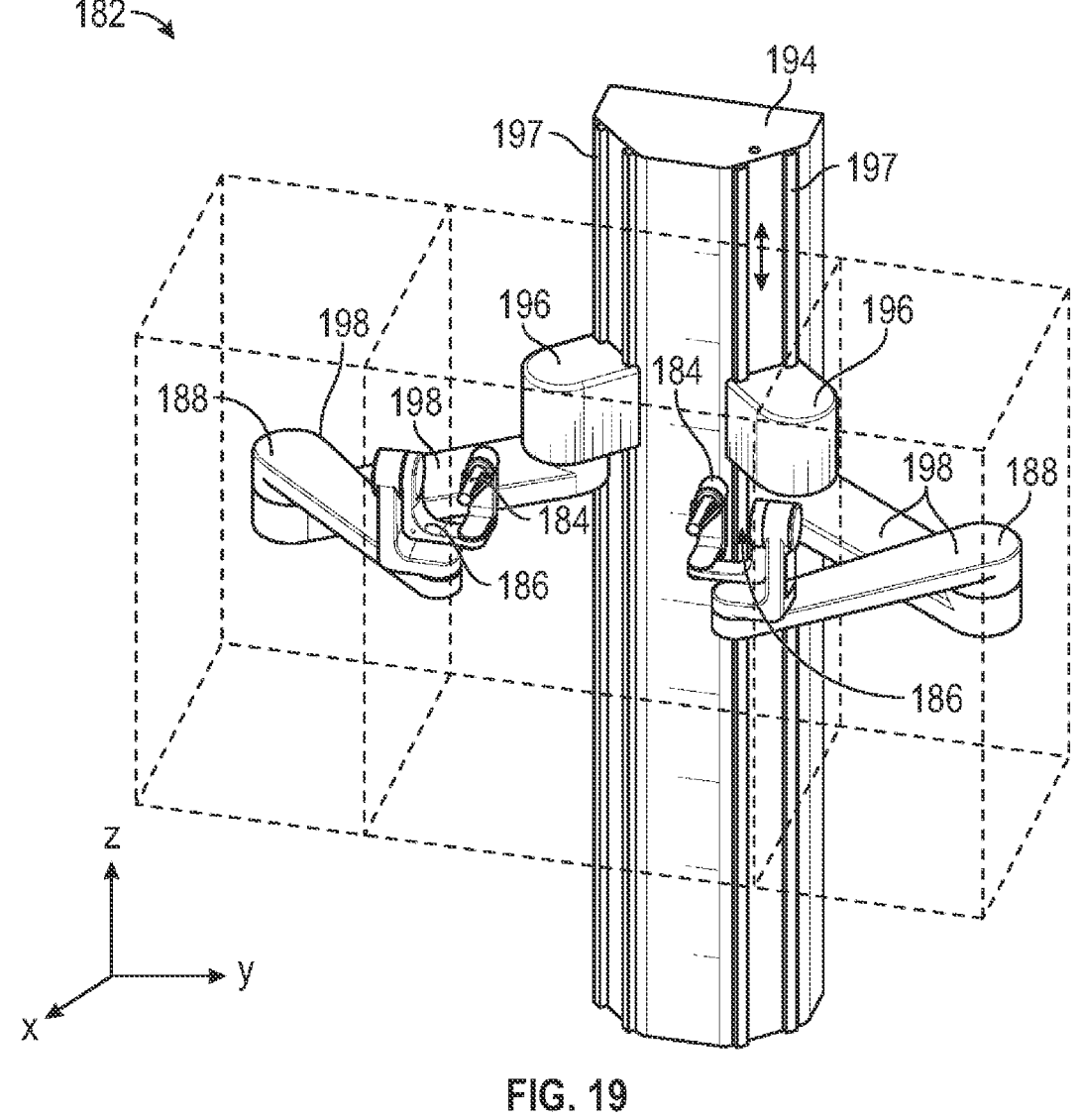
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
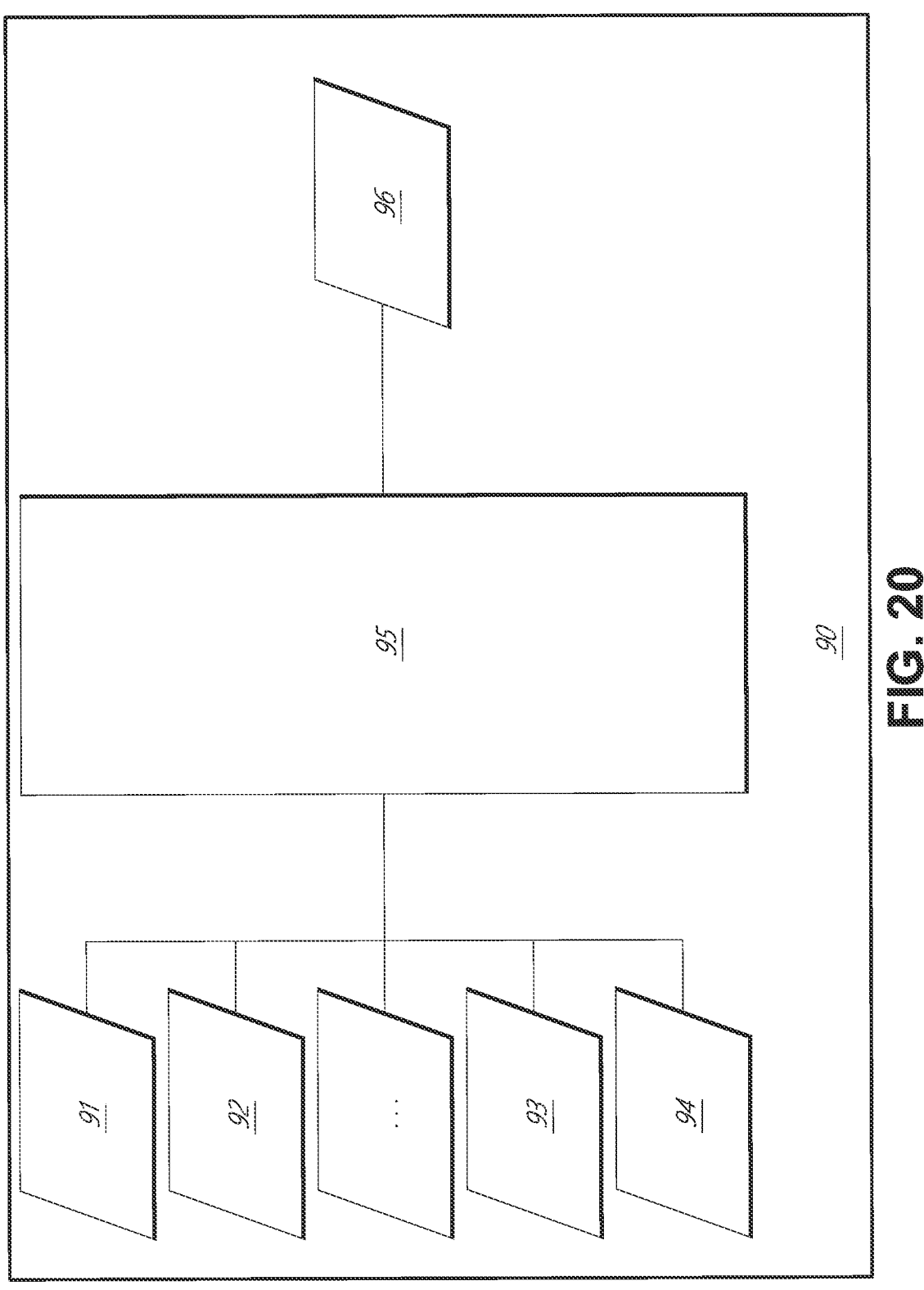
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, now issued as U.S. Pat. No. 9,763,741, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Transport of Surgical Systems

Some embodiments of the disclosure include systems related to surgical systems, and more particularly to systems for transporting and securing a surgical robotic system.

A console of a surgical robotic system, such as a physician's interface console, can include casters to allow the movement of the console. The casters may swivel to allow the console to be turned or otherwise maneuvered. In some applications, the swiveling functionality of certain conventional casters may allow the caster wheels to unintentionally swivel during forward or backward travel.

After transporting the console, the casters of the console can be stopped or otherwise locked into position prior to a surgical procedure to prevent inadvertent movement of the console. For example, the casters may be stopped to prevent movement of the console while a surgeon is operating the human interface devices (HIDs) of the console. In some applications, certain conventional consoles may only lock one caster wheel of the caster assembly. Further, in some applications, certain conventional consoles may not provide any indication of when a caster is locked or unlocked.

Caster assemblies disclosed herein can overcome one or more challenges discovered with respect to certain conventional caster assemblies. For example, in accordance with some embodiments disclosed herein, the present inventor's analysis led to the discovery of various realizations, deficiencies, and problematic features of prior art systems, some of which are presented herein, including the following realizations.

First, the present disclosure includes the realization that unintentional swiveling of the caster wheels can prevent a technician from easily or safely moving the console forwards or backwards without the console drifting laterally or wobbling. Further, certain conventional consoles with uneven distributions of mass may be more likely to laterally drift or wobble during transport. Additionally, certain conventional consoles may be designed and tested to be transported by a technician within a certain height and weight percentile, such that a technician's force is aligned with the center of mass of the console. Therefore, certain conventional consoles may be more likely to laterally drift or wobble during transport if transported by a technician that falls outside the design parameters (e.g. a technician that is shorter or lighter than the design criteria). Accordingly, some embodiments disclosed herein can provide caster assemblies having features that address one or more of these issues and minimize unintentional swiveling of the caster wheels. In some embodiments, the caster assembly described herein can implement a pedal actuated mechanism to selectively allow the caster wheels to freely swivel or rotate while locked in a desired alignment.

Second, the present disclosure includes the realization that locking a single caster wheel of a caster assembly may still allow the console to unintentionally move or be placed in an unstable state due to contact with the console during a surgical procedure or otherwise when a surgeon is interfacing with the console, which may also negatively affect a surgical procedure. Accordingly, some embodiments disclosed herein can provide caster assemblies having features that address one or more of these issues and securely position the console during a surgical procedure by locking multiple caster wheels. In some embodiments, the caster assembly described herein can implement a pedal actuated mechanism to selectively brake multiple caster wheels of the caster assembly simultaneously.

Third, the present disclosure includes the realization that because certain conventional consoles do not provide a status or indication if a caster wheel is locked or unlocked, an inexperienced user may operate or interface with the console without locking the casters, which may cause the console to move due to unintentional contact with the console and negatively affect the surgical procedure. Accordingly, some embodiments disclosed herein can provide caster assemblies having features that address one or more of these issues and provide an indication if the caster wheels are locked. In some embodiments the caster assembly can implement a system or method to detect the position of the pedal and/or the status of the brakes to determine if the caster wheels are locked or unlocked. In some embodiments, the caster assembly can implement a system or method to prevent the console from being used in a surgical operation until the console is locked into position and the caster wheels are locked.

Figure 21:
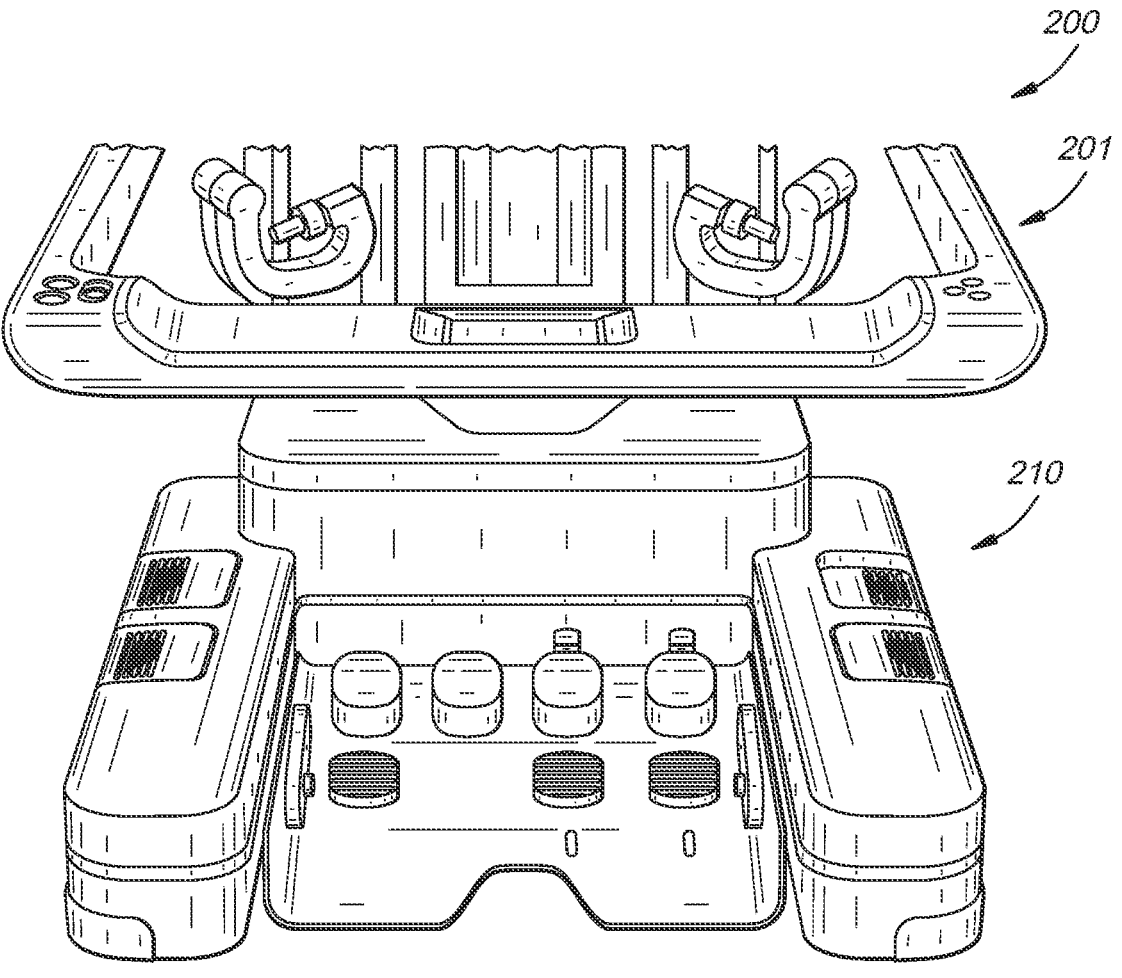
FIG. 21 illustrates a perspective view of a console.

FIG. 21 illustrates a perspective view of a console 200. In the depicted example, the console 200 can allow a surgeon or other clinician to perform a surgical procedure or otherwise control operations of a surgical robotic system. In some embodiments, the console 200 can be a physician's interface console that allows a surgeon to control operations of the surgical robotic system via one or more human interface devices 201. The console 200 may include features that are similar as features described with respect to console 31 herein.

Figure 22:
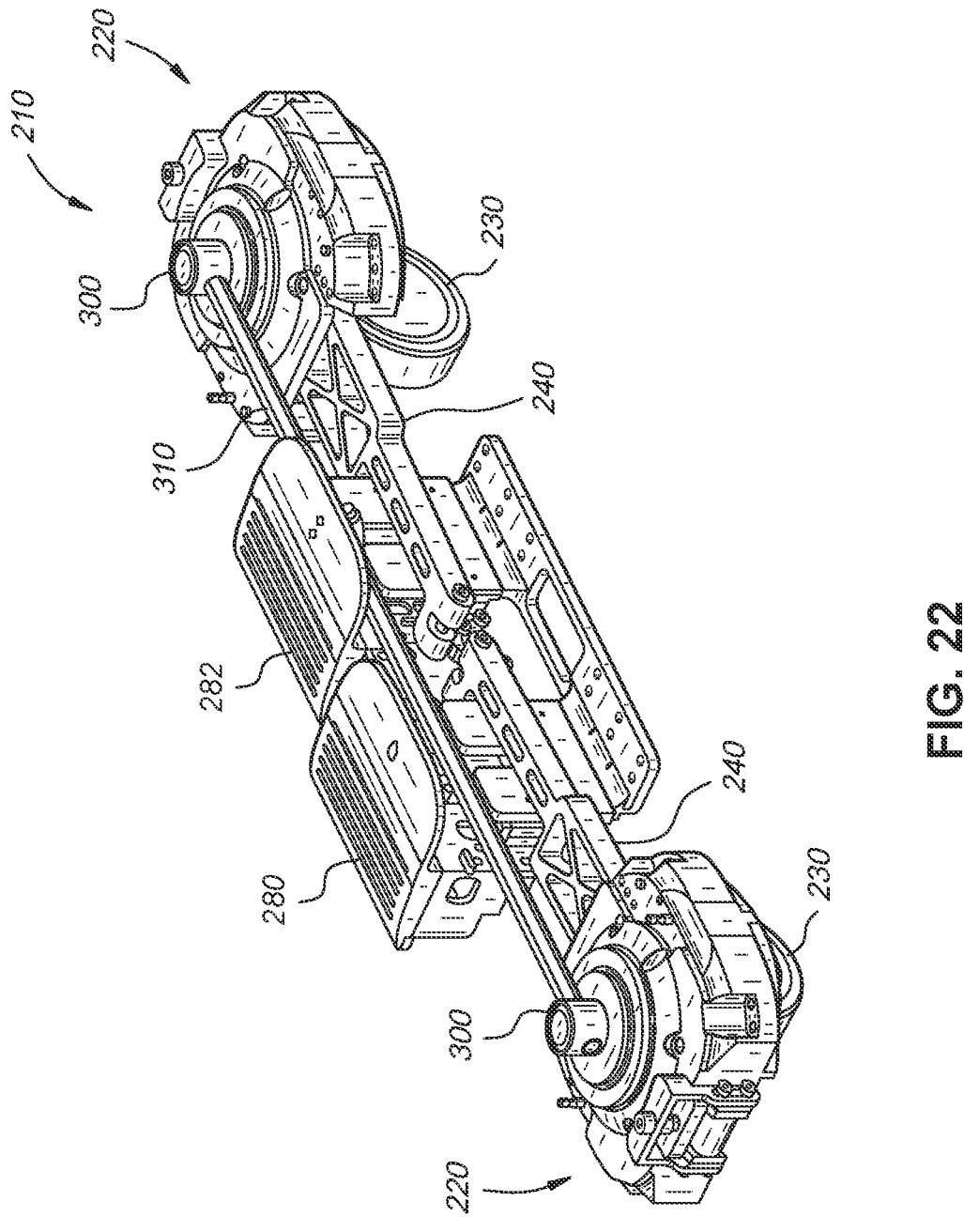
FIG. 22 illustrates a perspective view of a caster assembly.
Figure 23:
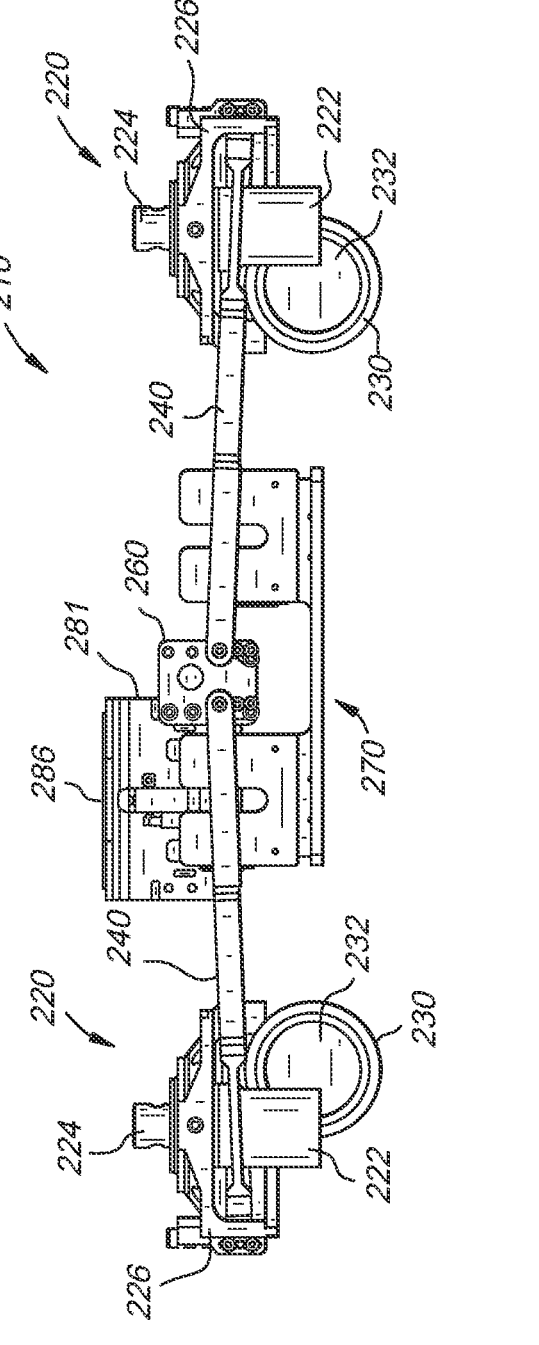
FIG. 23 illustrates a partial elevation view of the caster assembly of FIG. 22 with the lock members in an unlocked position.

FIG. 22 illustrates a perspective view of a caster assembly 210. FIG. 23 illustrates a partial elevation view of the caster assembly 210 of FIG. 22 with the lock members in an unlocked position. With reference to FIGS. 21-23, the console 200 includes one or more caster assemblies 210 that allow the console 200 to be transported between locations and secured for a surgical procedure and/or storage. In the depicted example, the console 200 can include a left caster assembly 210 and a right caster assembly 210 disposed on either side of the console 200 to allow transport and positioning of the console 200. As described herein, the caster assembly 210 includes at least two casters 220 that allow for the console 200 to be moved between locations.

In the depicted example, the caster wheel 230 rotates relative to a wheel housing 232, allowing the console 200 to be moved. As illustrated, the wheel housing 232 is coupled to the caster support 224 via a wheel support 222. In some embodiments, components of the caster 220 are further covered or obscured by a shroud 226. The caster support 224 can be coupled to the console 200 to secure the caster assembly 210 to the console 200.

Further, in embodiments, the caster wheels 230 may be able to swivel relative to the caster support 224 and the console 200 to allow the console 200 to be turned or maneuvered. In the depicted example, the wheel support 222 can be rotatably coupled to the caster support 224 to allow the wheel support 222 and in turn the caster wheel 230 to swivel relative to the caster support 224. In some embodiments, the caster wheel 230 can swivel within the shroud 226.

As described herein, the caster assembly 210 further includes locking members 240 to selectively brake or lock the caster wheels 230, securing the console 200 in a desired position. Further, the caster assembly 210 can include a direction locking mechanism 300 to selectively allow the caster wheels 230 to swivel for increased maneuverability or be locked in a desired alignment to allow the console 200 to be readily moved in a straight line. In the illustrated embodiment, the caster assembly 210 includes one or more pedal assemblies 280, 282 to control the operation of the locking members 240 and the direction locking mechanism 300, respectively.

Optionally, some embodiments of the caster assembly 210 can comprise one or more sensors that can detect the state of the pedal assembly 280 to determine the whether the caster wheels 230 are locked or unlocked. In some embodiments, the caster assembly 210 described herein can be used with any suitable console or component for use with a surgical robotic system.

Figure 24:
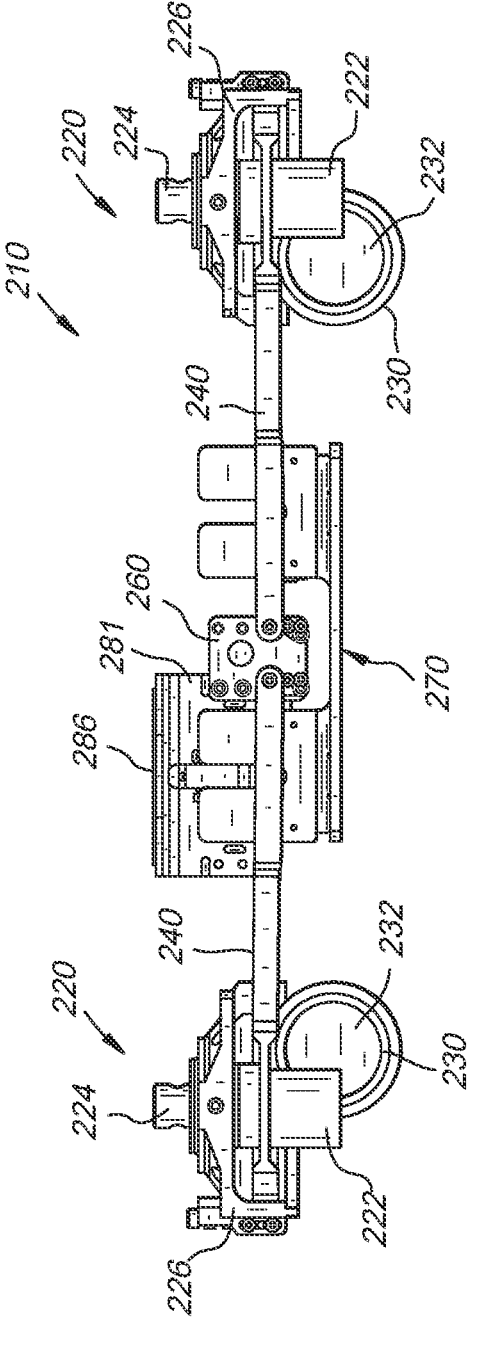
FIG. 24 illustrates a partial elevation view of the caster assembly of FIG. 22 with the lock members in a locked position.
Figure 25:
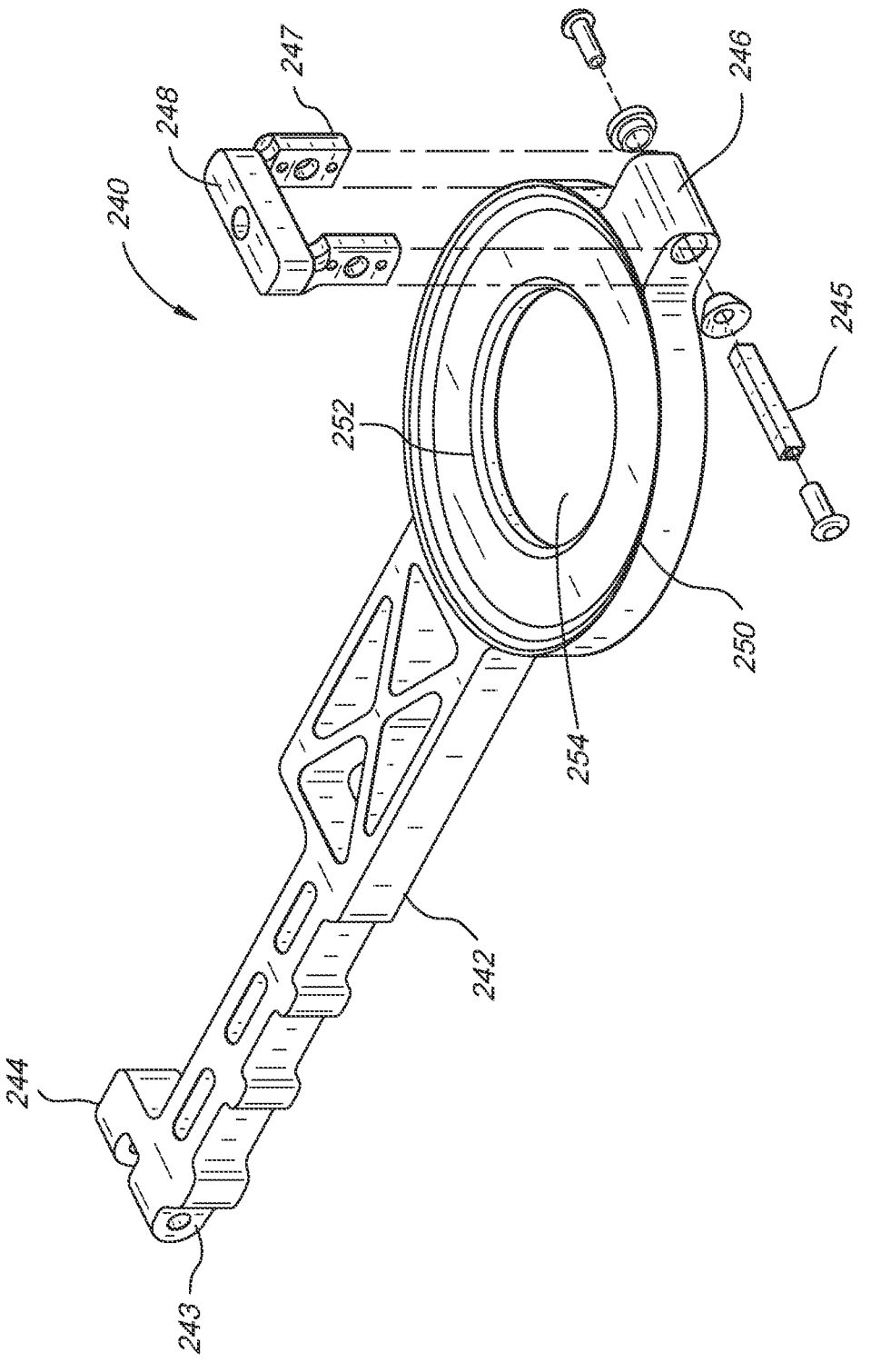
FIG. 25 illustrates an exploded perspective view of a lock member.

FIG. 24 illustrates a partial elevation view of the caster assembly of FIG. 22 with the lock members in a locked position. FIG. 25 illustrates an exploded perspective view of a lock member. With reference to FIGS. 23-25, the locking member 240 is movable to selectively engage with the caster wheel 230, braking or locking the caster wheel 230 in position. In the depicted example, the locking member 240 is movable between an unlocked position (FIG. 23) wherein the locking member 240 is spaced apart from the caster wheel 230 to allow the caster wheel 230 to freely rotate and a locked position (FIG. 24) where the locking member 240 engages with the caster wheel 230 with sufficient force to prevent rotation of the caster wheel 230 and/or prevent movement of an attached console. As described herein, multiple locking members 240 can selectively engage with multiple respective caster wheels 230 to control the rotation of each caster wheel 230.

In the depicted example, the locking member 240 includes a brake portion 252 configured to frictionally engage with the caster wheel 230 to slow or stop rotation. The brake portion 252 can be formed from a material configured to generate a desired frictional force when in contact with the caster wheel 230. As illustrated, the brake portion 252 can be formed as lock ring 250 with an opening 254 therethrough. Advantageously, the annular construction of the lock ring 250 can allow the wheel support 222 to pass through the opening 254, permitting the caster wheel 230 to swivel relative to the lock ring 250, while still allowing the brake portion 252 of the lock ring 250 to engage with the caster wheel 230 regardless of the swivel or rotational position of the caster wheel 230. In some embodiments, the lock ring 250 can have a generally circular profile. Optionally, the lock ring 250 can have an oval or egg shaped profile, which may permit an even distribution of braking force regardless of the swivel or rotational position of the caster wheel 230.

Figure 26:
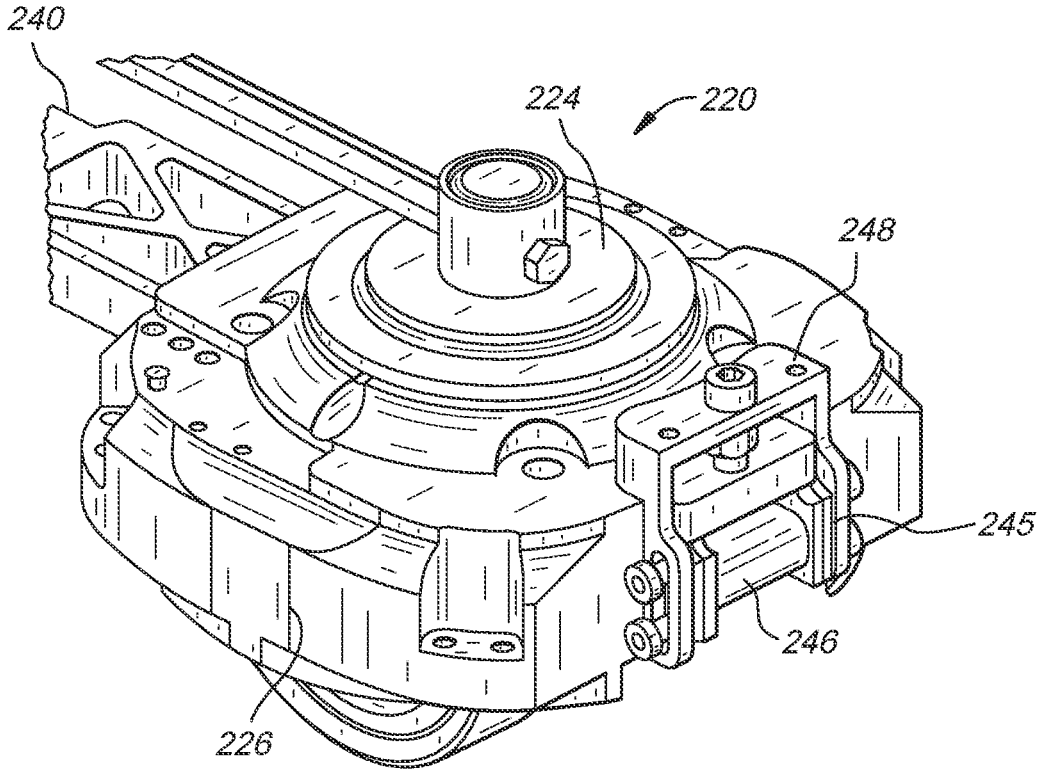
FIG. 26 illustrates a partial perspective view of the caster assembly of FIG. 22.

During operation, the brake portion 252 (or the lock ring 250, generally) can move relative to the caster wheel 230, engaging and/or disengaging the brake portion 252 from the caster wheel 230. FIG. 26 illustrates a partial perspective view of the caster assembly 210 of FIG. 22. With reference to FIGS. 25 and 26, the lock ring 250 can rotate about a pivot pin 245, permitting the brake portion 252 to rotate in and out of engagement with the caster wheel 230 about an axis of rotation defined by the pivot pin 245. As illustrated, the lock ring 250 defines a pivot component 246 to receive the pivot pin 245 and rotatably couple the lock ring 250 to the pivot pin 245.

In some embodiments, variances or tolerances in the caster assembly 210 may result in inconsistent or varying braking force applied by the brake portion 252 against the caster wheel 230. Optionally, the axis of rotation of the lock ring 250 can be adjusted relative to the caster wheel 230 to ensure that a consistent and/or desired force is applied by the brake portion 252 on each caster wheel 230. In the depicted example, the pivot pin 245 defining the axis of rotation of the lock ring 250 is captured or otherwise supported by a yoke 248 via legs 247. By adjusting or manipulating a vertical position of the yoke 248 relative to the caster wheel 230, the position of the pivot pin 245, and therefore the axis of rotation of the lock ring 250, is adjusted relative to the caster wheel 230. In some embodiments, the yoke 248 can be adjustably coupled to the shroud 226. The vertical position of the yoke 248 relative to the shroud 226 (and the caster wheel 230) may be adjusted by tightening or loosening an adjustment screw. The adjustment screw may include a lock nut to maintain the vertical position of the yoke 248 after adjustment.

In the depicted example, the brake portion 252 can be moved or rotated relative to the caster wheel 230 by applying force to or moving an extension portion 242 extending from the lock ring 250. As illustrated in at least FIG. 25, the extension portion 242 can extend from the lock ring 250 in a direction opposite to the pivot component 246. In some embodiments, an end portion 243 of the extension portion 242 can be moved to move or actuate the brake portion 252 relative to the caster wheel 230. Optionally, the length of the extension portion 242 and/or the position of the end portion 243 relative to the brake portion 252 can be configured to multiply the force applied by the user to the brake portion 252 by a desired factor. Similarly, the length of the extension portion 242 and/or the position of the end portion 243 relative to the brake portion 252 can be configured to adjust the travel required by the user to engage or disengage the brake portion 252 relative to the caster wheel 230.

Figure 27:
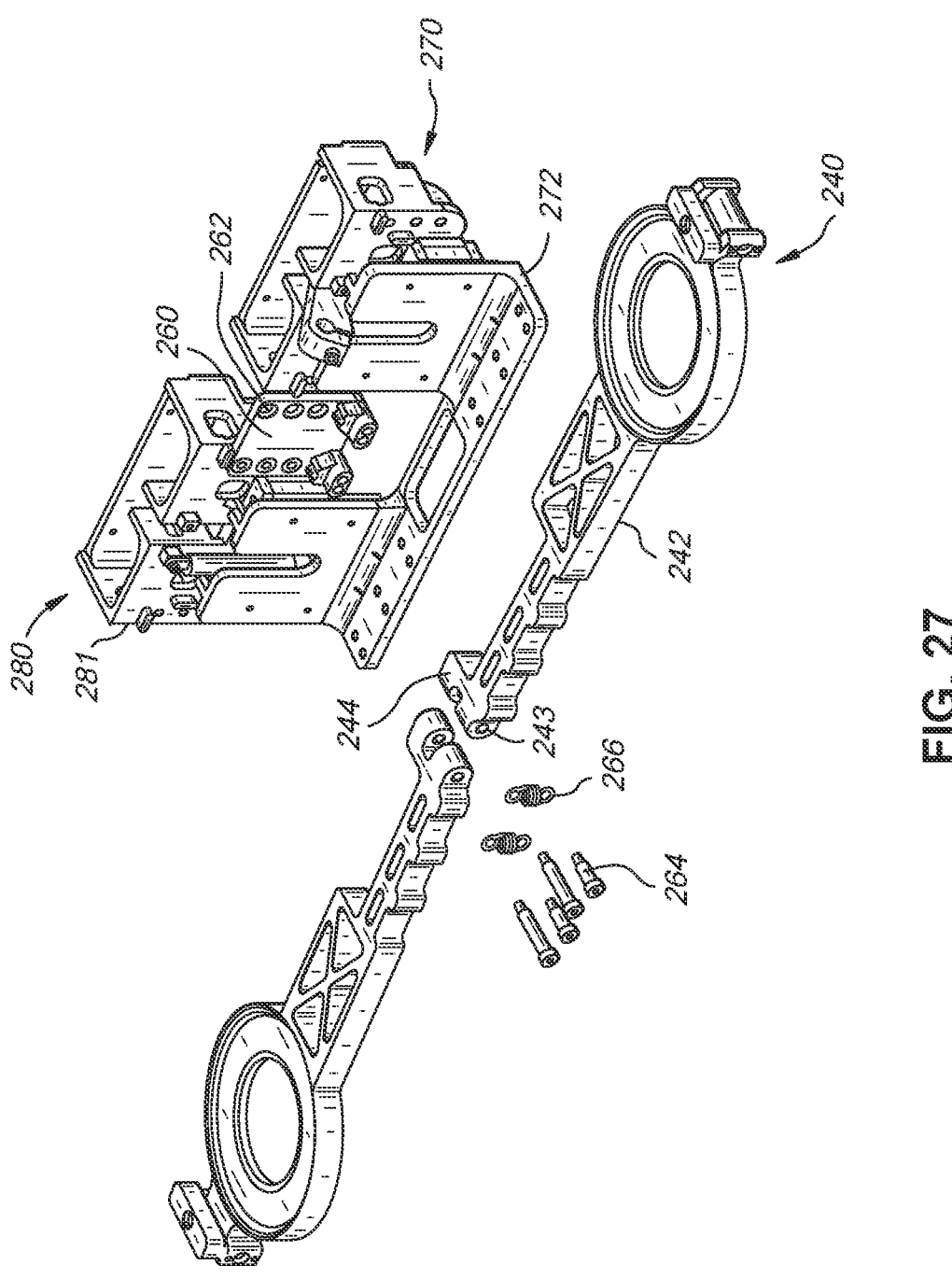
FIG. 27 illustrates a partial exploded perspective view of the lock members and the pedal assembly.

FIG. 27 illustrates a partial exploded perspective view of the lock members 240 and the pedal assembly 280. With reference to FIGS. 23-25, and 27, one or more lock members 240 can be moved or otherwise actuated by a lock plate 260 to engage or disengage the brake portion 252 relative to a caster wheel 230. As illustrated, multiple lock members 240 (e.g. two lock members 240) can be moved or actuated by a single common lock plate 260 to engage or disengage a brake portion 252 relative to a respective caster wheel 230. As illustrated in FIG. 23, the lock plate 260 can be moved upward to disengage the brake portion 252 of the respective lock member 240 from the respective caster wheel 230. As illustrated in FIG. 24, the lock plate 260 can be moved downward to engage the brake portion 252 of a respective lock member 240 against a respective caster wheel 230.

In some embodiments, an end portion 243 of each respective lock member 240 is coupled to the lock plate 260 via one or more fasteners 264 extending through holes 244 of the lock member 240 and holes 262 of the lock plate 260. During operation, the lock members 240 can rotate around the fasteners 264 and relative to the lock plate 260 as the lock plate 260 is translated. As described above, variances or tolerances in the caster assembly 210 may result in inconsistent or varying braking force applied by the brake portion 252 against the caster wheel 230.

In some embodiments, the amount of travel for the lock members 240 between the unlocked and locked position can change based on the swivel or rotational position of each caster wheel 230, since the rotational position of each caster wheel 230 may alter the point of contact or pivot location between the lock member 240 and the respective caster wheel 230. Therefore, in some embodiments, the lock members 240 can be coupled to the lock plate 260 via an extension spring 266 to correct for differences in travel between the unlocked and locked position as the swivel or rotational position of the caster wheels 230 is changed. During operation, the extension spring 266 can extend or contract relative to the lock plate 260 to adjust for the amount of travel needed to move the lock members 240 between the unlocked and locked positions depending on the swivel or rotational position of the respective caster wheel 230. Optionally, one end of the extension spring 266 may be coupled to the lock plate 260 via one or more fasteners 264 extending through holes 262 of the lock plate 260 and the other end of the extension spring 266 may be coupled to the end portion 243 of the lock member 240 via one or more fasteners 264 extending through holes 244 of the lock member.

Figure 28:
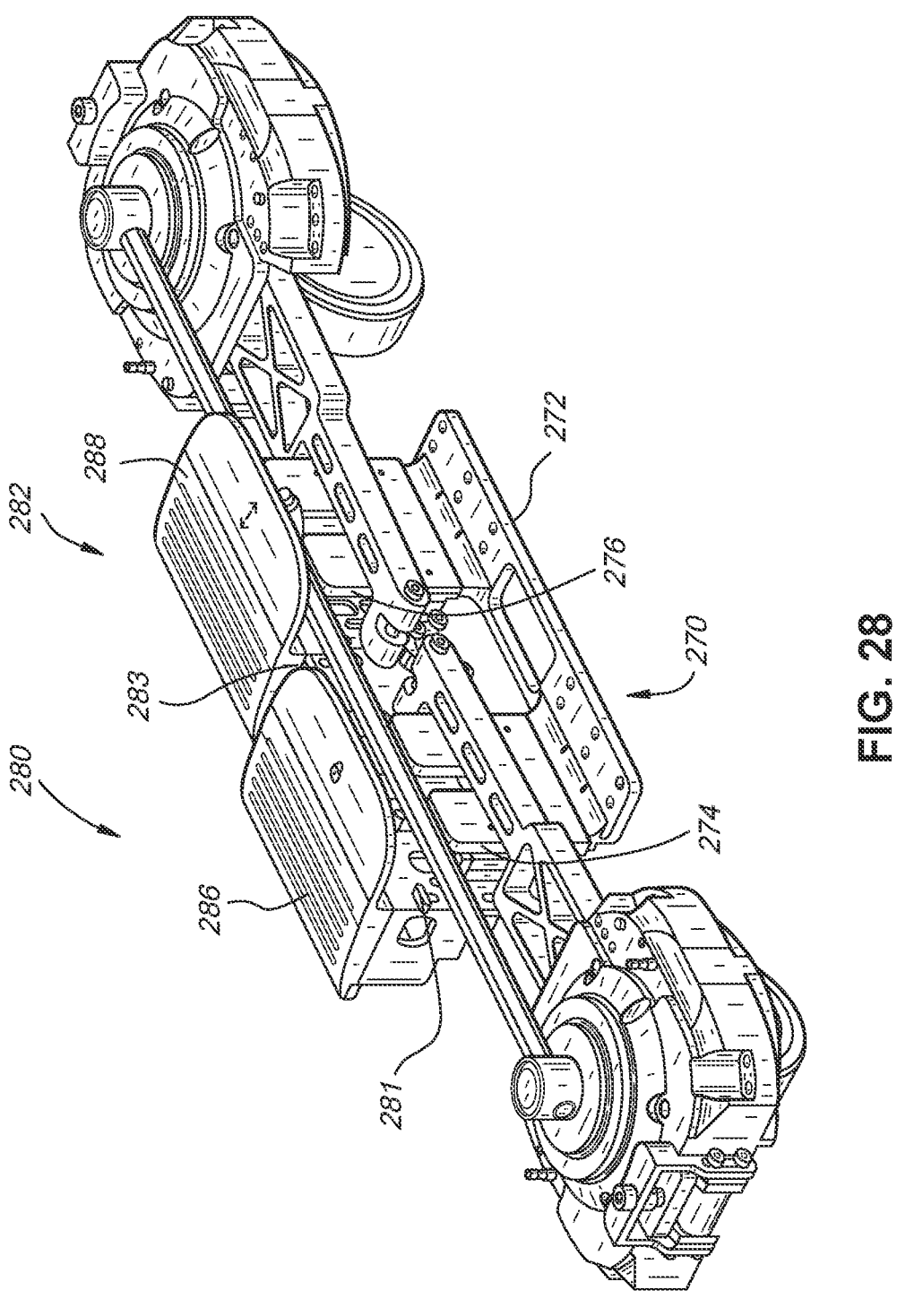
FIG. 28 illustrates a perspective view of a caster assembly.
Figure 29:
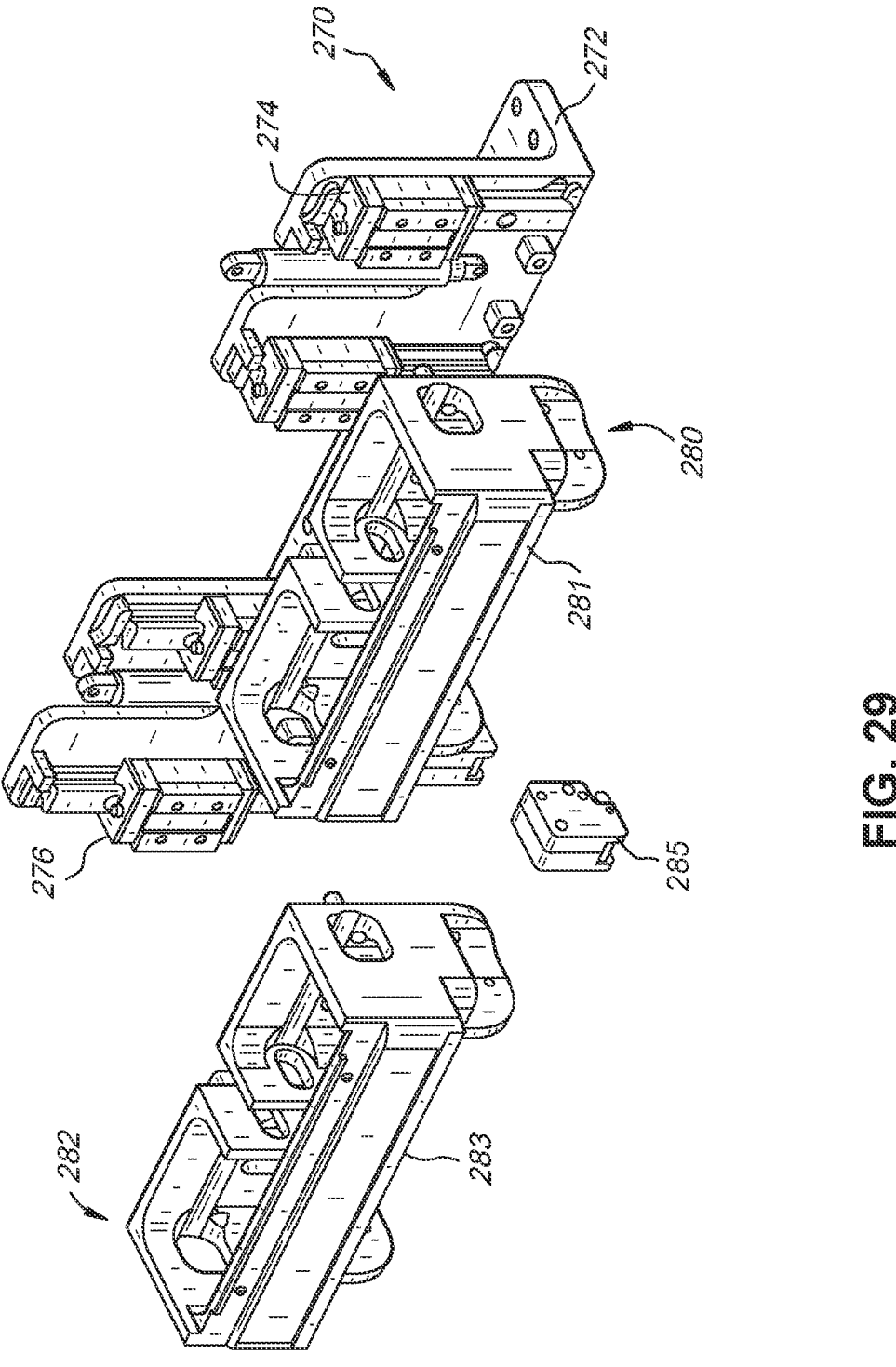
FIG. 29 illustrates a partial exploded perspective view of the pedal assemblies.
Figure 30:
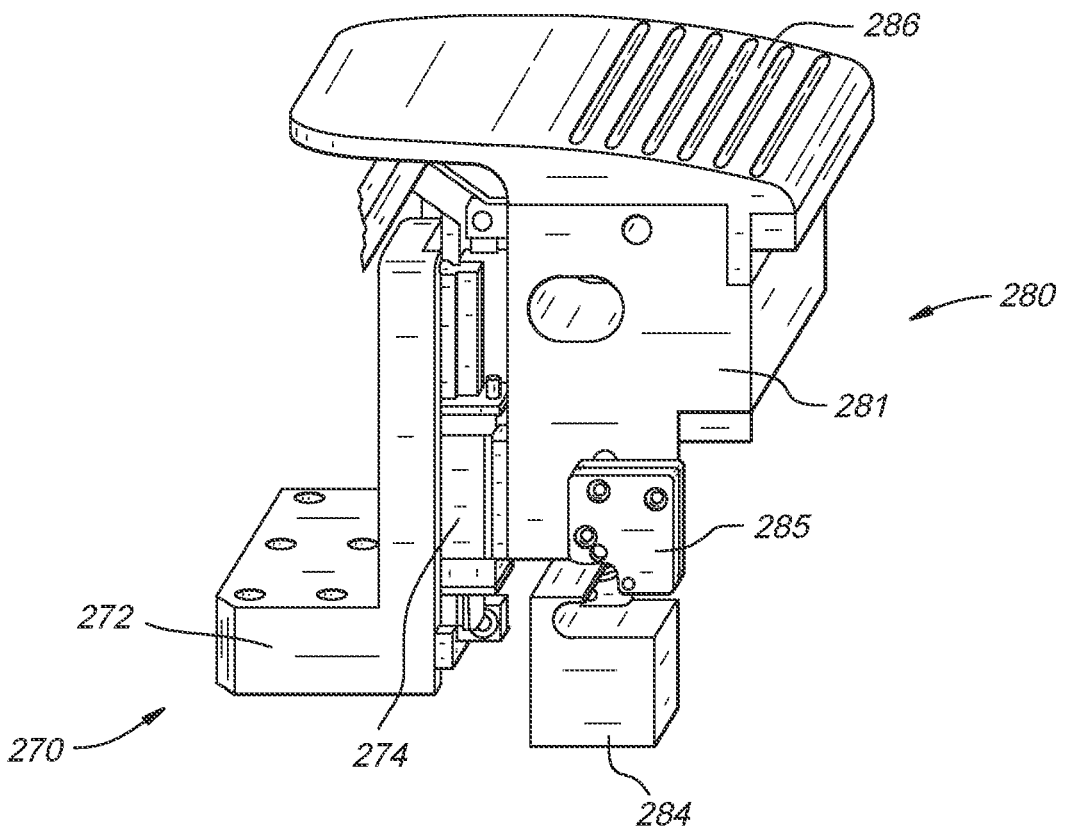
FIG. 30 illustrates a perspective view of a pedal assembly.
Figure 31:
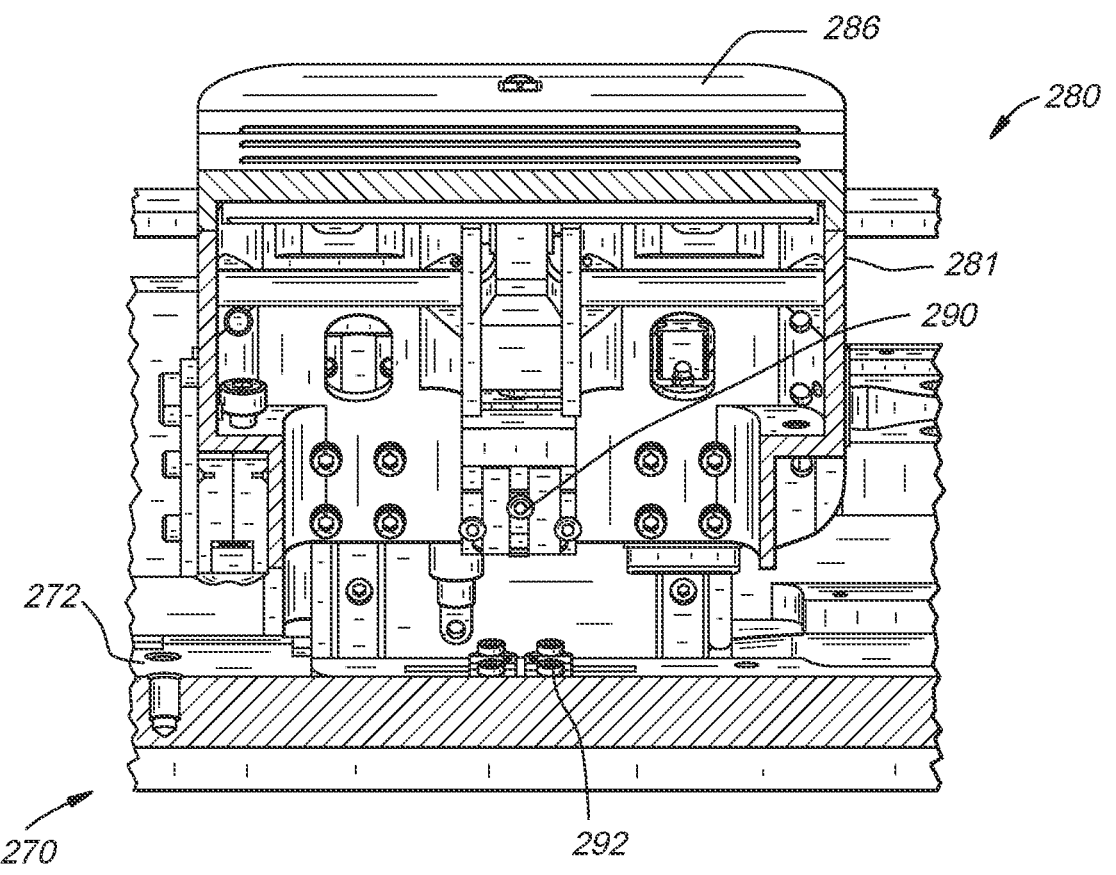
FIG. 31 illustrates a rear elevation view of the pedal assembly.

FIG. 28 illustrates a perspective view of a caster assembly 210. FIG. 29 illustrates a partial exploded perspective view of the pedal assemblies 280, 282. FIG. 30 illustrates a perspective view of a pedal assembly 280. FIG. 31 illustrates a rear elevation view of the pedal assembly 280.

With reference to FIGS. 28-31, the pedal assembly 280 allows a user to lock and unlock the caster wheels 230 of the caster assembly 210. In the depicted example, the pedal assembly 280 moves the lock plate 260 to control the position of the lock members 240, and in turn the brake portions 252 relative to the respective caster wheels 230. Advantageously, a user can selectively brake multiple caster wheels 230 simultaneously by actuating a single pedal assembly 280, preventing the console 200 from moving unintentionally or being placed in an unstable state during a surgical procedure or otherwise when a surgeon is interfacing with the console 200.

As illustrated, the pedal body 281 is coupled to the lock plate 260 to permit movement of the pedal body 281 to translate the lock plate 260. In the depicted example, the pedal body 281 is translatable or otherwise movable relative to the base frame 272 of the base assembly 270. In some embodiments, the pedal body 281 is coupled to the base frame 272 by a linear guide 274 to constrain the motion of the pedal body 281 to vertical translation. During operation, a user can depress the pedal body 281 by applying force to a pedal cover 286 affixed or otherwise coupled to a top portion of the pedal body 281. The pedal cover 286 can include a broad surface with one or more optional ridges to allow a user to easily step on the pedal cover 286 to depress or otherwise actuate the pedal assembly 280 and engage the brake portions 252 against the respective caster wheels 230. Optionally, a biasing member, such as a return spring can urge the pedal body 281 to an extended position and disengage the brake portions 252 from the respective caster wheels 230. In some embodiments, the return spring can be a gas spring.

In some embodiments, the pedal assembly 280 can include a latch 285 coupled to the pedal body 281 to retain the pedal body 281 (and therefore the lock plate 260) in a depressed or locked position. In the depressed position, the latch 285 can engage with the keep 284 coupled to the base frame 272 or other component that is stationary relative to the pedal body 281 to retain the pedal body 281 in the depressed position. In some embodiments, the engagement between the latch 285 and keep 284 is configured to overcome or withstand the return force from the biasing member to retain the pedal body 281 in the depressed position.

Optionally, the latch 285 can be disengaged from the keep 284 be further depressing the pedal body 281 relative to the keep 284, permitting the return force from the biasing member to return the pedal body 281 to the extended position.

In some embodiments, the caster assembly 210 can include one or more sensors to detect if the caster wheels 230 are locked or unlocked. Since the position of the pedal body 281 corresponds to the position of the brake portions 252 relative to the respective caster wheels 230, the position of the pedal body 281 can be utilized to determine if the caster wheels 230 are locked or unlocked. In the depicted example, the pedal assembly 280 may include one or more sensors 292 to detect the position of the pedal body 281 relative to the base frame 272. Sensors 292 may be coupled to the base frame 272 or disposed at any other suitable surface to detect the position of the pedal body 281. In some embodiments, the sensors 292 may include one or more hall effect sensors. Advantageously, the use of sensors 292 can be prevent a user from inadvertently interfacing with the console 200 without locking the caster wheels 230 in place, preventing the console 200 from moving during a surgical procedure. In some embodiments, both the left caster assembly 210 and the right caster assembly 210 can include sensors 292 to detect if the respective caster wheels 230 are locked or unlocked.

During operation, as the pedal body 281 is depressed or translated downward relative to the base frame 272, the sensors 292 may detect a change in magnetic field as the pedal body 281 is moved toward a locked position to determine the depressed position of the pedal body 281 and the locked state of the caster wheels 230. Similarly, the sensors 292 may detect a change in magnetic field as the pedal body 281 is translated upward to an unlocked position to determine the extended position of the pedal body 281 and the unlocked state of the caster wheels 230. In some embodiments, the pedal body 281 can include one, two, or more magnets 290 adhered, affixed, or otherwise coupled to the pedal body 281. In some embodiments, the pedal assembly 280 may include redundant sensors 292. The sensors 292 may include other suitable type of sensors including contact sensors, optical sensors, ultrasonic sensors, etc.

In some embodiments, information from the sensors 292 regarding the position of the pedal body 281 can be used to notify the user of the current lock state of the caster wheels 230 and/or prevent the use of the surgical robotic system while the caster wheels 230 are unlocked. In the depicted example, data from the sensors 292 can be provided to a controller of the robotic surgical system to provide a notification to the user that the caster wheels 230 are in a locked or unlocked state. In some embodiments, the robotic surgical system and/or the caster assembly 210 may provide an audible, visual, and/or tactile alert when the pedal body 281 is an extended position and/or the caster wheels 230 are in an unlocked state.

Optionally, the alert provided may be dependent on the operational status of the robotic surgical system. Further, in some embodiments, the robotic surgical system and/or the caster assembly 210 may prevent or disable surgical procedures when the pedal body 281 is an extended position and/or the caster wheels 230 are in an unlocked state. In some embodiments, the robotic surgical system may prevent or disable surgical procedures when caster wheels 230 of either the left or right caster assembly 210 are in an unlocked state. Similarly, the robotic surgical system and/or the caster assembly 210 may permit surgical procedures when the pedal body 281 is a depressed position and/or the caster wheels 230 are in a locked state. In some embodiments, the robotic surgical system may permit surgical procedures when the caster wheels 230 of both the left and right caster assemblies 210 are in a locked state.

Figure 32:
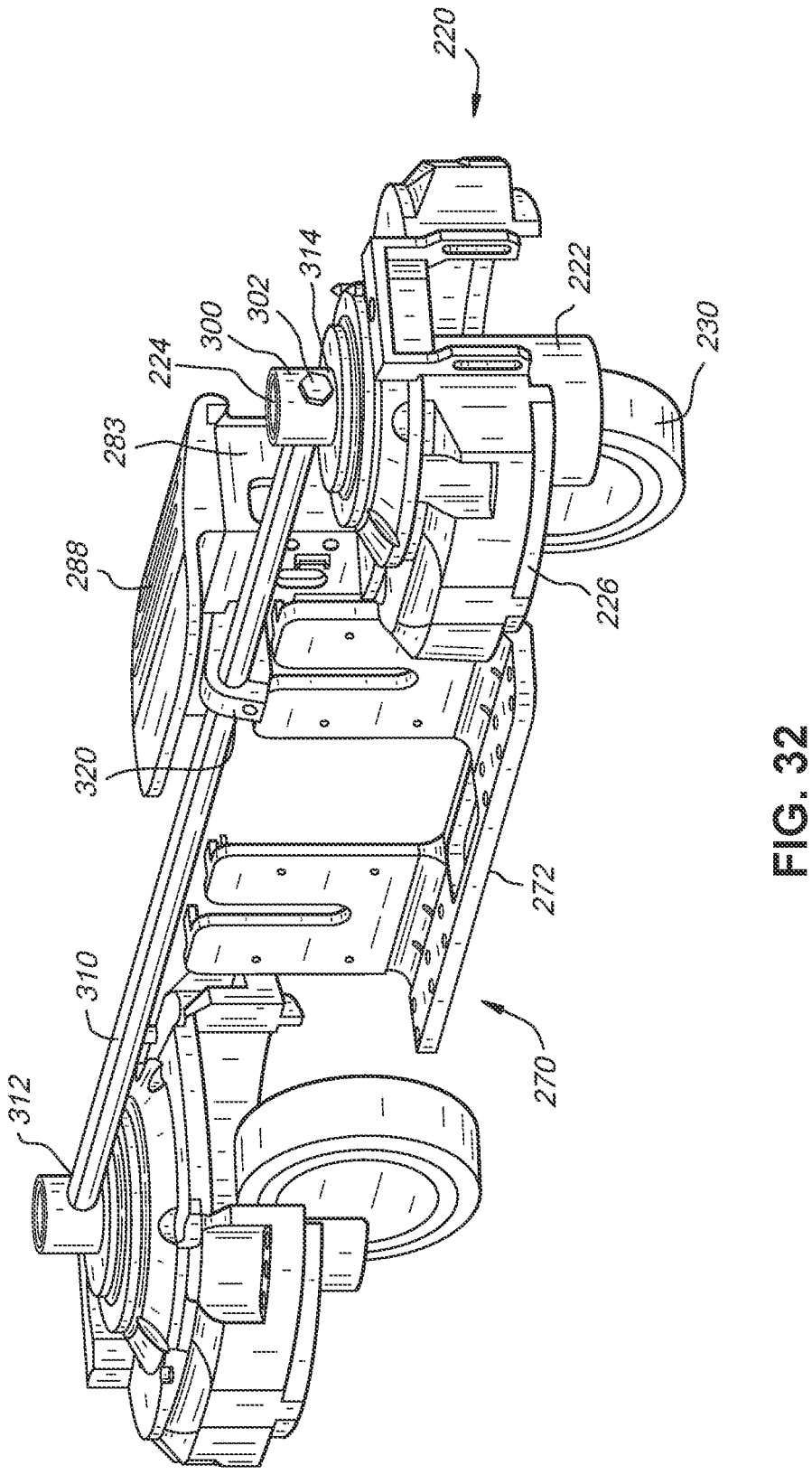
FIG. 32 illustrates a perspective view of a caster assembly with the direction locking mechanism unlocked.
Figure 33:
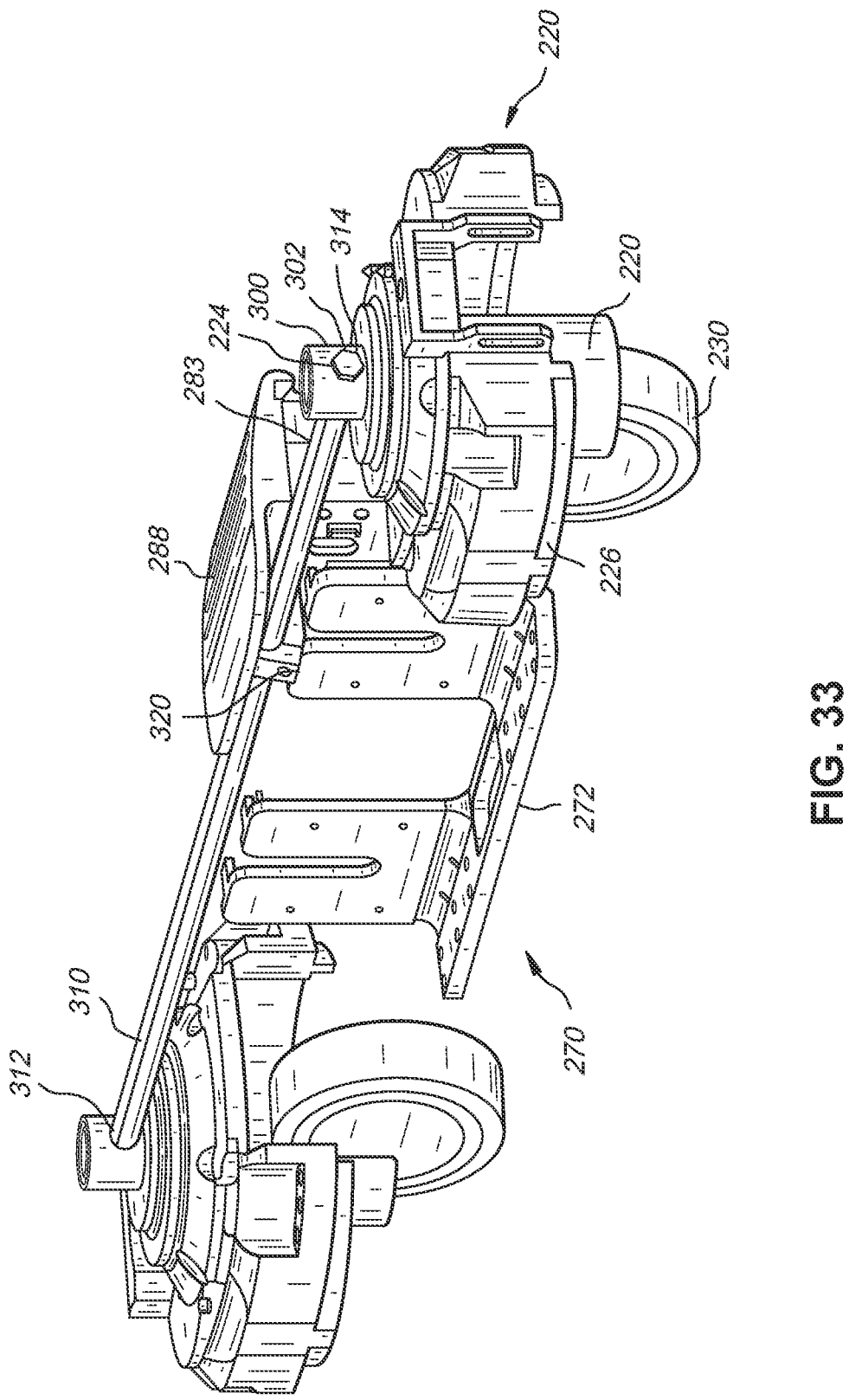
FIG. 33 illustrates a perspective view of a caster assembly with the direction locking mechanism locked.

FIG. 32 illustrates a perspective view of a caster assembly 210 with the direction locking mechanism 300 unlocked. FIG. 33 illustrates a perspective view of a caster assembly 210 with the direction locking mechanism 300 locked. With reference to FIGS. 32 and 33, the direction locking mechanism 300 can selectively allow the caster wheels 230 swivel or remain in a desired alignment. In the depicted example, the direction locking mechanism 300 is selectable between an unlocked position (FIG. 32) wherein the direction locking mechanism 300 allows the caster wheel 230 to freely swivel (and rotate relative to the wheel support 222), and a locked position (FIG. 33) wherein the direction locking mechanism 300 prevents the caster wheel 230 swiveling (without affecting the rotation of the caster wheel 230 relative to the wheel support 222). As described herein, multiple direction locking mechanisms 300 can be used selectively to control the swivel functionality of each caster wheel 230.

In some embodiments, the direction locking mechanism 300 selectively engages a raceway or other swiveling element of the caster wheel 230 to permit or prevent swiveling of the caster wheel 230. As described herein, a wheel support 222 of a caster wheel 230 can rotate relative to a caster support 224 to allow the caster wheel 230 to swivel. In some embodiments, the direction locking mechanism 300 can selectively engage or couple a wheel support 222 of a caster wheel 230 with a respective caster support 224 to permit or prevent swiveling of the caster wheel 230. In an unlocked position, the direction locking mechanism 300 can space apart, decouple, or otherwise disengage a wheel support 222 from the caster support 224 to allow the wheel support 222 to swivel independently of the caster support 224. In the locked position, the direction locking mechanism 300 can couple or engage the wheel support 222 with the caster support 224 to prevent the wheel support 222 from moving or swiveling independently of the caster support 224. In some embodiments, the direction locking mechanism 300 can use any suitable mechanism to permit or prevent swiveling of the caster wheel 230.

In some embodiments, the unlocked and the locked position of the direction locking mechanism 300 is selected by rotating a keyway 302. Optionally, the keyway 302 can be rotated a predetermined amount to select the locked position from an unlocked position, or vice versa. For example, the keyway 302 may be rotated 30 degrees to be moved from an unlocked position to a locked position or from the locked position to the unlocked position. As illustrated, the keyway 302 may be rotated by a hexagonal shaft or key 310 configured to interface with or apply a rotational force to the keyway 302.

In the depicted example, the keyway 302 of one or more direction locking mechanisms 300 can be operated or controlled from a spaced apart location via the key 310. As illustrated, the keyway 302 can be rotated by the first end 312 of the key 310 by applying torque to any part of the key 310, including the second end 314 or any other portion, including middle portions of the key 310. Similarly, a keyway 302 of a second direction locking mechanism 300 can be rotated by a second end 314 of the key by applying torque to any part of the key 310, including middle portions of the key 310. Therefore, in some embodiments, the key 310 can simultaneously rotate the keyway 302 of multiple direction locking mechanisms 300 via the first end 312 and the second end 314 of the key 310. Advantageously, by rotating the key 310 a user can simultaneously lock or unlock the direction locking mechanisms 300 corresponding to each caster wheel 230, allowing each caster wheel 230 to be simultaneously permitted to be swiveled or locked in a certain desired alignment.

Figure 34:
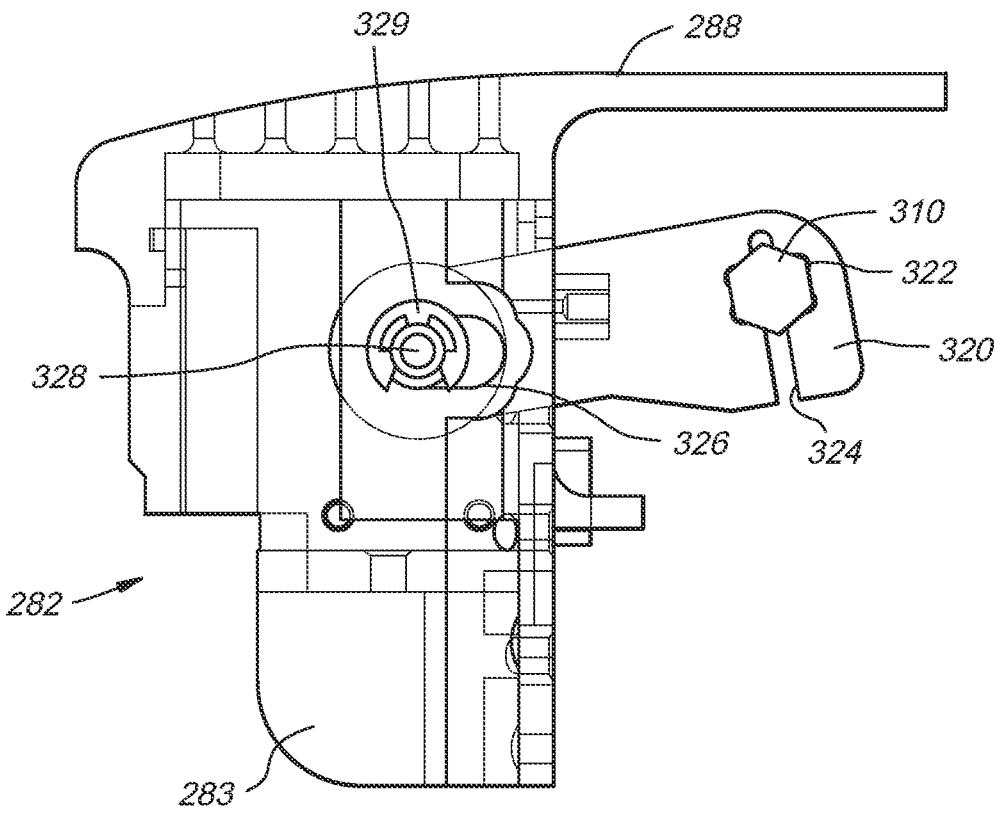
FIG. 34 illustrates a side elevation view of a direction locking pedal assembly.
Figure 35:
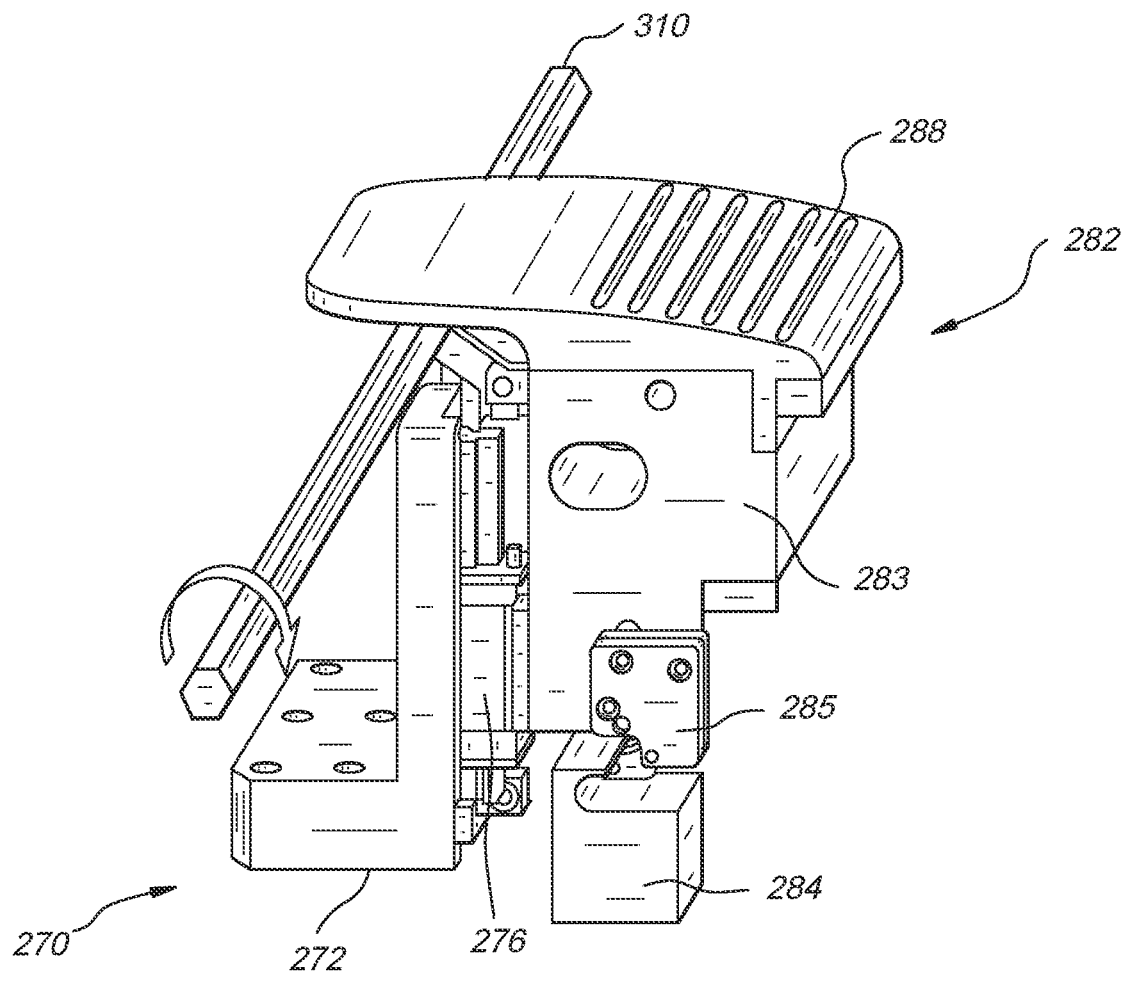
FIG. 35 illustrates a partial perspective view of a direction locking pedal assembly.

FIG. 34 illustrates a side elevation view of a direction locking pedal assembly 282. FIG. 35 illustrates a partial perspective view of a direction locking pedal assembly 282. With reference to FIGS. 34 and 35, the pedal assembly 282 allows a user to selectively permit and prevent swiveling of the caster wheels 230 of the caster assembly 210. In the depicted example, the pedal assembly 282 rotates the key 310 to move the keyway 302 of each direction locking mechanism 300 between an unlocked and locked position. Advantageously, a user can selectively allow the caster wheels 230 to freely swivel to permit maneuvering of a console 200 or lock the caster wheels 230 in a desired alignment to allow the console 200 to be moved forwards or backwards without the console 200 drifting laterally or wobbling.

As illustrated, the pedal body 283 is coupled to the key 310 via a linkage 320 to permit movement or translation of the pedal body 283 to rotate the key 310. In the depicted example, the pedal body 283 is translatable or otherwise movable relative to the base frame 272 of the base assembly 270. In some embodiments, the pedal body 283 is coupled to the base frame 272 by a linear guide 276 to constrain the motion of the pedal body 283 to vertical translation. As illustrated, the linkage 320 is coupled to the key 310 and is attached to the pedal body 283 via a rotatable linkage pivot component 328. Therefore, as the pedal body 283 translates vertically, the linkage 320 rotates relative to the pedal body 283, rotating the key 310. In the depicted example, moving the pedal body 283 downward rotates the linkage 320 downward and rotates the key 310 counter clockwise toward a lock position of the direction locking mechanism 300. Moving the pedal body 283 upward rotates the linkage 320 upward and rotates the key 310 clockwise toward an unlock position of the direction locking mechanism 300.

In some embodiments, the linkage 320 may be mated or otherwise coupled to the key 310 by a linkage keyway 322 formed in the linkage 320, permitting the linkage 320 to rotate the key 310. In some embodiments the linkage keyway 322 includes a key slot 324 to permit the insertion and removal of the key 310 from the linkage 320.

As illustrated, the linkage pivot component 328 may be disposed in an elongated slot 326 to allow the linkage pivot component 328 to travel in an arc as the linkage 320 rotates, preventing binding between the pedal body 283 and the linkage 320 as the pedal body 283 is translated. The linkage pivot component 328 may be captured or retained within the elongate slot 326 by a retaining clip 329.

During operation, a user can depress the pedal body 283 by applying force to a pedal cover 288 affixed or otherwise coupled to a top portion of the pedal body 283. The pedal cover 288 can include a broad surface with one or more optional ridges to allow a user to easily step on the pedal cover 288 to depress or otherwise actuate the pedal assembly 282 and lock the caster wheels 230 in a desired swivel orientation. In some embodiments, the pedal cover 288 corresponding to the operation of the direction locking mechanism 300 may be visually or tactilely differentiated from the pedal cover 286 corresponding to operation of the brake portions 252. Optionally, a biasing member, such as a return spring can urge the pedal body 283 to an extended position and permit the caster wheels 230 to freely swivel. In some embodiments, the return spring can be a gas spring.

Similar to pedal assembly 280, the pedal assembly 282 can include a latch 285 coupled to the pedal body 283 to retain the pedal body 283 (and therefore the key 310) in a depressed or locked position. In the depressed position, the latch 285 can engage with the keep 284 coupled to the base frame 272 or other component that is stationary relative to the pedal body 283 to retain the pedal body 283 in the depressed position. In some embodiments, the engagement between the latch 285 and keep 284 is configured to overcome or withstand the return force from the biasing member to retain the pedal body 283 in the depressed position. Optionally, the latch 285 can be disengaged from the keep 284 be further depressing the pedal body 283 relative to the keep 284, permitting the return force from the biasing member to return the pedal body 283 to the extended position.

3. Implementing Systems and Terminology

Implementations disclosed herein provide systems, methods and apparatus for operatively coupling an obturator and a cannula.

It should be noted that the terms "couple," "coupling," "coupled," or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present inventions. Various modifications to these implementations will be readily apparent to those skilled in the art, and the generic principles defined herein may be applied to other implementations without departing from the scope of the inventions. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present inventions are not intended to be limited to the implementations shown herein but is to be accorded the widest scope consistent with the principles and novel features disclosed herein.

What is claimed is:

1. A caster assembly for use with a surgical console, the caster assembly comprising:

a caster wheel;

a lock member that is engageable against the caster wheel, the lock member having a first end portion that defines a pivot and a second end portion that is movable to rotate the lock member about the pivot to selectively engage the lock member against the caster wheel;

a pedal coupled to the second end portion of the lock member, wherein (i) movement of the pedal towards a depressed position causes rotation of the lock member for engaging the lock member against the caster wheel to resist or prevent rotation of the caster wheel, and (ii) movement of the pedal towards a released position causes rotation of the lock member for separating the lock member from the caster wheel to permit rotation of the caster wheel;

a position sensor disposed adjacent to the pedal to detect a position of the pedal; and a controller configured to:

receive, from the position sensor, data indicative of an unlocked state of the caster wheel; and disable the surgical console from controlling one or more operations of a surgical robot in response to receiving the data indicative of the unlocked state of the caster wheel.

2. The caster assembly of claim 1, wherein the position sensor comprises a hall effect sensor.

3. The caster assembly of claim 2, further comprising a magnet coupled to the pedal, wherein the hall effect sensor detects the position of the magnet relative to the hall effect sensor.

4. The caster assembly of claim 1, comprising a second position sensor disposed adjacent to the pedal to detect the position of the pedal.

5. The caster assembly of claim 1, wherein the controller is further configured to permit to control the one or more operations in response to receiving data from the position sensor indicative of a locked state of the caster wheel.

6. The caster assembly of claim 1, further comprising a movable lock plate coupled the pedal and the second end portion of the lock member, wherein the movable lock plate is translatable with the pedal to rotate the lock member.

7. The caster assembly of claim 1, further comprising a linear guide coupled to the pedal, wherein the linear guide prevents lateral movement of the pedal.

8. The caster assembly of claim 1, further comprising a gas spring coupled to the pedal, wherein the gas spring is configured to urge the pedal toward the released position.

9. The caster assembly of claim 1, further comprising a latching mechanism configured to selectively retain the pedal in the depressed position.

10. A method of interlocking a surgical console, the method comprising:

detecting a position of a pedal that is coupled to a lock member of a caster assembly, wherein (i) movement of the pedal toward a locked position causes rotation of the lock member for engaging the lock member against a caster wheel to resist or prevent rotation of the caster wheel, and (ii) movement of the pedal toward an unlocked position causes rotation of the lock member for separating the lock member from the caster wheel to permit rotation of the caster wheel; and in response to the pedal being detected in the unlocked position, disabling the surgical console from controlling operation of a surgical robot; and in response to the pedal being detected in the locked position, enabling the surgical console to control operation of the surgical robot.

11. The method of claim 10, further comprising detecting a magnetic field of a magnet coupled to the pedal to determine the position of the pedal.

12. A caster assembly for use with a surgical console, the caster assembly comprising:

a caster, comprising:

a caster wheel configured for swiveling relative to the surgical console and for rotation relative to the surgical console independent of the swiveling; and a direction locking mechanism comprising a keyway that is rotatable to (i) a direction locked position for imparting resistance against the swiveling of the caster wheel relative to the surgical console, and to (ii) a direction unlocked position for permitting the swiveling of the caster wheel relative to the surgical console;

a key extending between a first end portion and a second end portion, wherein the first end portion extends through the keyway of the direction locking mechanism of the caster;

a first pedal rotatably coupled to the key, wherein the first pedal is movable (i) towards a first depressed position for rotating the key and the keyway toward the direction locked position in which the swiveling of the caster wheel is resisted, and (ii) towards a first released position for rotating the key and the keyway toward the direction unlocked position in which the rotation of the caster wheel is permitted;

a lock member defining a first end portion and a second end portion, and the second end portion of the lock member being pivotable about the first end portion;

a second pedal coupled to the second end portion of the lock member, wherein the second pedal is moveable independently of the first pedal (i) towards a second depressed position for rotating the lock member to engage the lock member against the caster wheel such that the rotation of the caster wheel is resisted, and (ii) towards a second released position for rotating the lock member to separate the lock member from the caster wheel such that the rotation of the caster wheel is permitted; and a position sensor disposed adjacent to the second pedal to detect a position of the second pedal and determine a rotational position of the lock member.

13. The caster assembly of claim 12, wherein the second pedal is disposed adjacent to the first pedal.

14. The caster assembly of claim 12, wherein the position sensor comprises a hall effect sensor.

15. The caster assembly of claim 14, further comprising a magnet coupled to the second pedal, wherein the hall effect sensor detects the position of the magnet relative to the hall effect sensor.

16. The caster assembly of claim 12, comprising a second position sensor disposed adjacent to the second pedal to detect the position of the second pedal.

17. The caster assembly of claim 12, further comprising a controller configured to:

receive the position of the second pedal from the position sensor; and disable an operation of the surgical console in response to the second pedal being detected in the second released position.

18. The caster assembly of claim 17, wherein the controller is further configured to permit operation of the surgical console in response to the second pedal being detected in the second depressed position.

19. The caster assembly of claim 1, wherein:

the surgical console includes a human interface device manipulatable by a user to cause a corresponding manipulation of an instrument by a robotic arm of the surgical robot, and the controller is configured to prevent the human interface device from causing the corresponding manipulation of the instrument by the robotic arm in response to the data indicative of the unlocked state.

20. The caster assembly of claim 19, wherein the controller is configured to:

receive, from the position sensor, data indicative of a locked state of the caster wheel; and permit the human interface device to cause the corresponding manipulation of the instrument by the robotic arm in response to receiving the data indicative of the locked state of the caster wheel.

* * * * *